United States Patent [19]

Nuyens et al.

[11] Patent Number: 5,919,913
[45] Date of Patent: *Jul. 6, 1999

[54] ISOLATION OF LACTOFERRIN FROM MILK

[75] Inventors: Jan H. Nuyens, MV Ileiloo; Harry H. Van Veen, NB Boskoop, both of Netherlands

[73] Assignee: Pharming B.V., Leiden, Netherlands

[ * ] Notice: This patent is subject to a terminal disclaimer.

[21] Appl. No.: 08/406,271

[22] Filed: Mar. 9, 1995

Related U.S. Application Data

[63] Continuation of application No. 08/198,321, Feb. 16, 1994, abandoned.

[51] Int. Cl.$^6$ .............................. C07K 14/79; C07K 1/18; C07K 1/22; A61K 38/40
[52] U.S. Cl. ...................... 530/395; 530/400; 530/413; 530/416; 530/832
[58] Field of Search ................................. 530/395, 400, 530/413, 416, 832; 800/2, DIG. 1; 536/127; 210/690, 691, 692, 908

[56] References Cited

U.S. PATENT DOCUMENTS

| | | | |
|---|---|---|---|
| 4,436,658 | 3/1984 | Peyrouset et al. | 530/387.1 |
| 4,668,771 | 5/1987 | Kawakami et al. | 530/366 |
| 4,791,193 | 12/1988 | Okonogi et al. | 530/416 |
| 4,977,137 | 12/1990 | Nichols et al. | 514/6 |
| 4,997,914 | 3/1991 | Kawakami et al. | 530/395 |
| 5,149,647 | 9/1992 | Burling | 435/192 |
| 5,240,909 | 8/1993 | Nitsche | 514/8 |

FOREIGN PATENT DOCUMENTS

| | | |
|---|---|---|
| 0 253 395 B1 | 10/1991 | European Pat. Off. |
| WO 89/04608 | 6/1989 | WIPO |
| 9108216 | 6/1991 | WIPO |
| WO 91/08216 | 6/1991 | WIPO |

OTHER PUBLICATIONS

Houdebine "Production of Pharmaceutica Proteins from Transgenic Animals" J. Biotechnol. 34 269–287, 1994.

Wall "Transgenic Livestock: Progress & Prospects for the Future" Therigenology 45 57–68, 1996.

Hennighausen et al. "Regulation of Expression of Genes for Milk Proteins", 1990.

Bezwoda et al. (1986) *Clin. Chem. Acta.* 157:89–94 Isolation and characterisation of lactoferrin separated from human whey by absorption chromatography using Cibacron Blue F3G–A linked affinity absorbent.

Blackberg (1980) *FEBS Lett.* 109:180–184 Isolation of lactoferrin from human whey by a single chromatographic step.

Chen et al. (1991) *J. Food Sci.* 56:701–706 Microfiltration affinity purification of lactoferrin and immunoglobulin G from cheese whey.

Ekstrand et al. (1986) *Jour. of Chromatography* 358:429–433 Fast protein liquid chromatography of antibacterial components in milk. Lactoperoxidase, lactoferrin and lysozyme.

Foley et al. (1987) *Anal. Biochem.* 162:296–300 The purification of lactoferrin from human whey by batch extraction.

Hutchens et al. (1989) *Clin. Chem.* 35:1928–1933 Purification and characterization of intact lactoferrin found in the urine of human milk–fed preterm infants.

Johnson (1969) *Acta Chem. Scand.* 23:683–714 Isolation of crystalline lactoferrin from human milk.

Johnson et al. (1958) *Nature.* 181:996–997 Chromatographic separation of lactalbumin from human milk whey on calcium phosphate columns.

Kawakami et al. (1987) *J. Dairy Sci.* 70:752–759 One step isolation of lactoferrin using immobilized monoclonal antibodies.

Metz–Boutigue et al. (1984) *Eur J. Biochem.* 145:659–676 Human lactotransferrin: amino acid sequence and structural comparisons with other transferrins.

Moguilevsky et al. (1985) *Biochem J.* 229:353–359 Comparisons of human lactoferrins from milk and neutrophilic leucocytes.

Pentecost et al. (1987) *J. Biol. Chem.* 262:10134–10139 Lactotransferrin is the major estrogen inducible protein of mouse uterine secretions.

Querinjean et al. (1971) *Eur. J. Biochen.* 20:420–25 Molecular weight, single–chain structure and amino acid composition of human lactoferrrin.

Roberts et al. (1975) *Jour. of Reproductive Fertility.* 42:579–582 The isolation and characterization of lactoferrin from sow milk and boar seminal plasma.

Shimazaki et al. (1993) *Int. J. Biochem.* No. 11, 25:1653–1658 Analysis of human and bovine milk lactoferrins by rotofor and chromatofocusing.

Torres et al. (1979) *Biochem. Biophys. Acta.* 576:385–392 Fraction of granule proteins of granulocytes by copper chelate chromatography.

Yoshida (1991) *J. Dairy Sci.* 74:1439–1444 Isolation of lactoperoxidase and lactoferrins from bovine milk acid whey by carboxymethyl cation exchange chromatography.

Zagulski et al. (1979) *Prace i Materialy Zootechniczne.* 20:87–103 A simple method of obtaining large quantities of bovine lactoferrin.

Shimazaki et al. "Analysis of Human & Bovine Milk Lactoferrins by Rotofor & Chromatofocusing" Int J Biochem 15(11) 1653–1658 1993.

(List continued on next page.)

Primary Examiner—Nancy Degen
Attorney, Agent, or Firm—Townsend & Townsend & Crew

[57] ABSTRACT

The invention provides methods for purification of human lactoferrin from milk, especially milk of nonhuman species, and for separation of human lactoferrin from undesired macromolecular species present in the milk, including separation from nonhuman lactoferrin species.

27 Claims, 13 Drawing Sheets

OTHER PUBLICATIONS

Alcantara et. al. "The N–Linked Oligosaccharides of Human Lactoferrin are not Required for Binding to Bacterial Lactoferrin Receptors" Can. J. Microbiol. 38 1202–1205 1992.

Clark "Prospects for the Genetic Engineering of Milk" J. Cell Biochem 49 121–127 1992.

Krimpenfurt et. al. "Expression of Biomedical Proteins in Milk of Transgenic Animals" J. Cell. Biochem Supp 15A 201 1991.

Shimazaki etal Int J Biochem 25(11) 1653–1658 1993.

Alcantara et al Can J. Microbiol. 38 1202–1205 1992.

Clark J Cell Biochem 49 121–127 1992.

Krimpenfurt et al. J Cell Biochem Supp 15A 201 1991

SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
       (A) LENGTH: 25 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Peptide
       (B) LOCATION: 1..25
       (D) OTHER INFORMATION: /note= "HLF GPE 1"

(xi) SEQUENCE DESCRIPTION: SEQ ID NO:1:

Gly Arg Arg Arg Arg Ser Val Gln Trp Xaa Ala Val Ser Gln Pro Glu
   1               5                   10                  15

Ala Thr Lys Xaa Phe Gln Trp Gln Arg
               20                  25

(2) INFORMATION FOR SEQ ID NO:2:

(i) SEQUENCE CHARACTERISTICS:
       (A) LENGTH: 54 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Peptide
       (B) LOCATION: 1..54
       (D) OTHER INFORMATION: /note= "HLF cDNA of GPE"

(xi) SEQUENCE DESCRIPTION: SEQ ID NO:2:

Gly Arg Arg Arg Arg Ser Val Gln Trp Cys Ala Val Ser Gln Pro Glu
   1               5                   10                  15

Ala Thr Lys Cys Phe Gln Trp Gln Arg Asn Met Arg Lys Val Arg Gly
               20                  25                  30

Pro Pro Val Ser Cys Ile Lys Arg Asp Ser Pro Ile Gln Cys Ile Gln
               35                  40                  45

Ala Ile Ala Glu Asn Arg
           50

(2) INFORMATION FOR SEQ ID NO:3:

(i) SEQUENCE CHARACTERISTICS:
       (A) LENGTH: 18 amino acids
       (B) TYPE: amino acid
       (C) STRANDEDNESS: Not Relevant
       (D) TOPOLOGY: Not Relevant (ii) MOLECULE TYPE: peptide (ix) FEATURE:
       (A) NAME/KEY: Peptide
       (B) LOCATION: 1..18
       (D) OTHER INFORMATION: /note= "apoE"

(xi) SEQUENCE DESCRIPTION: SEQ ID NO:3:

Leu Arg Val Arg Leu Ala Ser His Leu Arg Lys Leu Arg Lys Arg Leu

```
                1           5            10            15

Leu Arg (2) INFORMATION FOR SEQ ID NO:4:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..30
        (D) OTHER INFORMATION: /note= "HLF M.B."

(xi) SEQUENCE DESCRIPTION: SEQ ID NO:4:

Gly Arg Arg Arg Arg Ser Val Gln Trp Cys Ala Val Ser Gln Pro Glu
        1               5                  10                  15

Ala Thr Lys Cys Phe Gln Trp Gln Ser Asn Val Arg Arg Met
                    20                  25                  30

(2) INFORMATION FOR SEQ ID NO:5:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..53
        (D) OTHER INFORMATION: /note= "HLF cDNA Rado"

(xi) SEQUENCE DESCRIPTION: SEQ ID NO:5:

Gly Arg Arg Arg Ser Val Gln Trp Cys Ala Val Ser Asn Pro Glu Ala
        1               5                  10                  15

Thr Lys Cys Phe Gln Trp Gln Arg Asn Met Arg Lys Val Arg Gly Pro
                    20                  25                  30

Pro Val Ser Cys Leu Lys Arg Asp Ser Pro Ile Gln Cys Ile Gln Ala
                    35                  40                  45

Ile Ala Glu Asn Arg
                    50

(2) INFORMATION FOR SEQ ID NO:6:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..47
        (D) OTHER INFORMATION: /note= "Lactoferricin H"

(xi) SEQUENCE DESCRIPTION: SEQ ID NO:6:

Gly Arg Arg Arg Arg Ser Val Gln Trp Cys Ala Val Ser Gln Pro Glu
        1               5                  10                  15

Ala Thr Lys Cys Phe Gln Trp Gln Arg Asn Met Arg Lys Val Arg Gly
```

```
                      20                  25                  30

Pro Pro Val Ser Cys Ile Lys Arg Asp Ser Pro Ile Gln Cys Ile
                35                  40                  45

(2) INFORMATION FOR SEQ ID NO:7:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..23
        (D) OTHER INFORMATION: /note= "Lactoferricin H synthetic analog"

(xi) SEQUENCE DESCRIPTION: SEQ ID NO:7:

Thr Lys Xaa Phe Gln Trp Gln Arg Asn Met Arg Lys Val Arg Gly Pro
    1               5                   10                  15

Pro Val Ser Xaa Ile Lys Asp
                20

(2) INFORMATION FOR SEQ ID NO:8:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..25
        (D) OTHER INFORMATION: /note= "Lactoferricin B"

(xi) SEQUENCE DESCRIPTION: SEQ ID NO:8:

Phe Lys Cys Arg Arg Trp Gln Trp Arg Met Lys Lys Leu Gly Ala Pro
    1               5                   10                  15

Ser Ile Thr Cys Val Arg Arg Ala Phe
                20                  25

(2) INFORMATION FOR SEQ ID NO:9:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..25
        (D) OTHER INFORMATION: /note= "Lactoferricin B synthetic analog"

(xi) SEQUENCE DESCRIPTION: SEQ ID NO:9:

Phe Lys Xaa Arg Arg Trp Gln Trp Arg Met Lys Lys Leu Gly Ala Pro
    1               5                   10                  15

Ser Ile Thr Xaa Val Arg Arg Ala Phe
                20                  25

(2) INFORMATION FOR SEQ ID NO:10:
```

(i) SEQUENCE CHARACTERISTICS:
    (A) LENGTH: 8 amino acids
    (B) TYPE: amino acid
    (C) STRANDEDNESS: Not Relevant
    (D) TOPOLOGY: Not Relevant (ii) MOLECULE TYPE: peptide (ix) FEATURE:
    (A) NAME/KEY: Peptide
    (B) LOCATION: 1..8
    (D) OTHER INFORMATION: /note= "Calbio. peak III"

(xi) SEQUENCE DESCRIPTION: SEQ ID NO:10:

Gly Arg Arg Arg Arg Ser Val Gln
1               5

(2) INFORMATION FOR SEQ ID NO:11:

(i) SEQUENCE CHARACTERISTICS:
    (A) LENGTH: 11 amino acids
    (B) TYPE: amino acid
    (C) STRANDEDNESS: Not Relevant
    (D) TOPOLOGY: Not Relevant (ii) MOLECULE TYPE: peptide (ix) FEATURE:
    (A) NAME/KEY: Peptide
    (B) LOCATION: 1..11
    (D) OTHER INFORMATION: /note= "Calbio. peak II"

(xi) SEQUENCE DESCRIPTION: SEQ ID NO:11:

Arg Arg Arg Ser Val Gln Trp Xaa Ala Val Ser
1               5                   10

(2) INFORMATION FOR SEQ ID NO:12:

(i) SEQUENCE CHARACTERISTICS:
    (A) LENGTH: 11 amino acids
    (B) TYPE: amino acid
    (C) STRANDEDNESS: Not Relevant
    (D) TOPOLOGY: Not Relevant (ii) MOLECULE TYPE: peptide (ix) FEATURE:
    (A) NAME/KEY: Peptide
    (B) LOCATION: 1..11
    (D) OTHER INFORMATION: /note= "Calbio. peak I"

(xi) SEQUENCE DESCRIPTION: SEQ ID NO:12:

Arg Arg Ser Val Gln Trp Xaa Ala Val Ser Gln
1               5                   10

(2) INFORMATION FOR SEQ ID NO:13:

(i) SEQUENCE CHARACTERISTICS:
    (A) LENGTH: 9 amino acids
    (B) TYPE: amino acid
    (C) STRANDEDNESS: Not Relevant
    (D) TOPOLOGY: Not Relevant (ii) MOLECULE TYPE: peptide (ix) FEATURE:
    (A) NAME/KEY: Peptide
    (B) LOCATION: 1..9
    (D) OTHER INFORMATION: /note= "HLF GPE 2 peak III"

(xi) SEQUENCE DESCRIPTION: SEQ ID NO:13:

Gly Arg Arg Arg Arg Ser Val Gln Trp
1               5

(2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..15
        (D) OTHER INFORMATION: /note= "Trans HLF GPE 1"

(xi) SEQUENCE DESCRIPTION: SEQ ID NO:14:

Gly Arg Arg Arg Arg Ser Val Gln Trp Xaa Ala Val Ser Gln Pro
1               5                   10                  15

(2) INFORMATION FOR SEQ ID NO:15:

(i) SEQUENCE CHARACTERISTICS:
        (A) LENGTH: 21 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..21
        (D) OTHER INFORMATION: /note= "Trans HLF GPE 2"

(xi) SEQUENCE DESCRIPTION: SEQ ID NO:15:

Gly Arg Arg Arg Arg Ser Val Gln Trp Xaa Ala Val Ser Gln Pro Glu
1               5                   10                  15

Ala Lys Xaa Phe Gln
            20

(2) INFORMATION FOR SEQ ID NO:16:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..22
        (D) OTHER INFORMATION: /note= "MLF GPE"

(xi) SEQUENCE DESCRIPTION: SEQ ID NO:16:

Lys Ala Thr Thr Val Arg Trp Xaa Ala Val Ser Asn Ser Glu Glu
1               5                   10                  15

Lys Xaa Leu Arg Trp Gln
            20

(2) INFORMATION FOR SEQ ID NO:17:

(i) SEQUENCE CHARACTERISTICS:
        (A) LENGTH: 52 amino acids
        (B) TYPE: amino acid
        (C) STRANDEDNESS: Not Relevant
        (D) TOPOLOGY: Not Relevant (ii) MOLECULE TYPE: peptide

```
    (ix) FEATURE:
         (A) NAME/KEY: Peptide
         (B) LOCATION: 1..52
         (D) OTHER INFORMATION: /note= "MLF cDNA Teng"

(xi) SEQUENCE DESCRIPTION: SEQ ID NO:17:

Lys Ala Thr Thr Val Arg Trp Cys Ala Val Ser Asn Ser Glu Glu Glu
    1               5                  10                  15

Lys Cys Leu Arg Trp Gln Asn Glu Met Arg Lys Val Gly Gly Pro Pro
                 20                  25                  30

Leu Ser Cys Val Lys Lys Ser Ser Thr Arg Gln Cys Ile Gln Ala Ile
                 35                  40                  45

Val Thr Asn Arg
        50

(2) INFORMATION FOR SEQ ID NO:18:

(i) SEQUENCE CHARACTERISTICS:
         (A) LENGTH: 14 amino acids
         (B) TYPE: amino acid
         (C) STRANDEDNESS: Not Relevant
         (D) TOPOLOGY: Not Relevant (ii) MOLECULE TYPE: peptide (ix) FEATURE:
         (A) NAME/KEY: Peptide
         (B) LOCATION: 1..14
         (D) OTHER INFORMATION: /note= "MDF"

(xi) SEQUENCE DESCRIPTION: SEQ ID NO:18:

Lys Ala Val Arg Val Gln Trp Xaa Ala Val Ser Asn Glu Glu
    1               5                  10

(2) INFORMATION FOR SEQ ID NO:19:

(i) SEQUENCE CHARACTERISTICS:
         (A) LENGTH: 18 amino acids
         (B) TYPE: amino acid
         (C) STRANDEDNESS: Not Relevant
         (D) TOPOLOGY: Not Relevant (ii) MOLECULE TYPE: peptide (ix) FEATURE:
         (A) NAME/KEY: Peptide
         (B) LOCATION: 1..18
         (D) OTHER INFORMATION: /note= "MTF Sigma"

(xi) SEQUENCE DESCRIPTION: SEQ ID NO:19:

Val Pro Asp Lys Thr Val Lys Trp Xaa Ala Val Xaa Glu His Xaa Asn
    1               5                  10                  15

Ile Lys (2) INFORMATION FOR SEQ ID NO:20:

(i) SEQUENCE CHARACTERISTICS:
         (A) LENGTH: 49 amino acids
         (B) TYPE: amino acid
         (C) STRANDEDNESS: Not Relevant
         (D) TOPOLOGY: Not Relevant (ii) MOLECULE TYPE: peptide (ix) FEATURE:
         (A) NAME/KEY: Peptide
         (B) LOCATION: 1..49
         (D) OTHER INFORMATION: /note= "HTF DNA"
```

(xi) SEQUENCE DESCRIPTION: SEQ ID NO:20:

Val Pro Asp Lys Thr Val Arg Trp Cys Ala Val Ser Glu His Glu Ala
1               5                   10                  15

Thr Lys Cys Gln Ser Phe Arg Asp His Met Lys Ser Val Ile Pro Ser
                20                  25                  30

Asp Gly Pro Ser Val Ala Cys Val Lys Lys Ala Ser Tyr Leu Asp Cys
            35                  40                  45

Ile (2) INFORMATION FOR SEQ ID NO:21:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..25
        (D) OTHER INFORMATION: /note= "HTF M.B."

(xi) SEQUENCE DESCRIPTION: SEQ ID NO:21:

Gly Arg Arg Arg Arg Ser Val Gln Trp Cys Ala Val Ser Gln Met Glu
1               5                   10                  15

Ala Thr Lys Cys Glu Ser Phe Arg Asp
                20                  25

(2) INFORMATION FOR SEQ ID NO:22:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1..53
        (D) OTHER INFORMATION: /note= "BLF cDNA Pier ce"

(xi) SEQUENCE DESCRIPTION: SEQ ID NO:22:

Ala Pro Arg Lys Asn Val Arg Trp Cys Thr Ile Ser Gln Pro Glu Trp
1               5                   10                  15

Phe Lys Cys Arg Arg Trp Gln Trp Arg Met Lys Lys Leu Gly Ala Pro
                20                  25                  30

Ser Ile Thr Cys Val Arg Arg Ala Phe Ala Leu Glu Cys Ile Arg Ala
            35                  40                  45

Ile Ala Glu Lys Lys
        50

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide

```
          (B) LOCATION: 1..5
          (D) OTHER INFORMATION: /note= "BLF Banyard"

(xi) SEQUENCE DESCRIPTION: SEQ ID NO:23:

Ile Ala Gln Pro Glu
   1               5

(2) INFORMATION FOR SEQ ID NO:24:

(i) SEQUENCE CHARACTERISTICS:
          (A) LENGTH: 11 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Peptide
          (B) LOCATION: 1..11
          (D) OTHER INFORMATION: /note= "BTF Banyard"

(xi) SEQUENCE DESCRIPTION: SEQ ID NO:24:

Asp Pro Glu Arg Thr Val Arg Trp Cys Thr Ile
   1               5                  10

(2) INFORMATION FOR SEQ ID NO:25:

(i) SEQUENCE CHARACTERISTICS:
          (A) LENGTH: 29 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Peptide
          (B) LOCATION: 1..29
          (D) OTHER INFORMATION: /note= "OLF"

(xi) SEQUENCE DESCRIPTION: SEQ ID NO:25:

Ala Pro Arg Lys Asn Val Arg Trp Cys Ala Ile Ser Pro Glu Gly
   1               5                  10                  15

Ser Arg Cys Tyr Gln Trp Gln Lys Lys Met Arg Arg Met
                   20                  25

(2) INFORMATION FOR SEQ ID NO:26:

(i) SEQUENCE CHARACTERISTICS:
          (A) LENGTH: 30 amino acids
          (B) TYPE: amino acid
          (C) STRANDEDNESS: Not Relevant
          (D) TOPOLOGY: Not Relevant (ii) MOLECULE TYPE: peptide (ix) FEATURE:
          (A) NAME/KEY: Peptide
          (B) LOCATION: 1..30
          (D) OTHER INFORMATION: /note= "OTF"

(xi) SEQUENCE DESCRIPTION: SEQ ID NO:26:

Ala Pro Pro Lys Ser Val Arg Ile Trp Cys Thr Ile Ser Pro Glu
   1               5                  10                  15

Glu Lys Lys Cys Asn Asn Leu Arg Asp Leu Thr Gln Gln Glu
                   20                  25                  30

(2) INFORMATION FOR SEQ ID NO:27:
```

```
        (i) SEQUENCE CHARACTERISTICS:
            (A) LENGTH: 47 amino acids
            (B) TYPE: amino acid
            (C) STRANDEDNESS: Not Relevant
            (D) TOPOLOGY: Not Relevant (ii) MOLECULE TYPE: peptide (ix) FEATURE:
            (A) NAME/KEY: Peptide
            (B) LOCATION: 1..47
            (D) OTHER INFORMATION: /note= "PLF"

(xi) SEQUENCE DESCRIPTION: SEQ ID NO:27:

Ala Pro Lys Lys Gly Val Arg Trp Cys Val Ile Ser Thr Ala Glu Tyr
       1               5                  10                  15

Ser Lys Cys Arg Gln Trp Gln Ser Lys Ile Arg Arg Thr Asn Pro Ile
                   20                  25                  30

Phe Cys Ile Arg Arg Ala Ser Pro Thr Asp Cys Ile Arg Ala Ile
                   35                  40                  45

(2) INFORMATION FOR SEQ ID NO:28:

(i) SEQUENCE CHARACTERISTICS:
            (A) LENGTH: 17 amino acids
            (B) TYPE: amino acid
            (C) STRANDEDNESS: Not Relevant
            (D) TOPOLOGY: Not Relevant (ii) MOLECULE TYPE: peptide (ix) FEATURE:
            (A) NAME/KEY: Peptide
            (B) LOCATION: 1..17
            (D) OTHER INFORMATION: /note= "PTF"

(xi) SEQUENCE DESCRIPTION: SEQ ID NO:28:

Ala Gln Lys Thr Val Arg Trp Cys Thr Ile Ser Asn Gln Glu Ala Asn
       1               5                  10                  15

Lys
```

ISOLATION OF LACTOFERRIN FROM MILK

This is a Continuation of application Ser. No. 08/198,321, filed Feb. 16, 1994, now abandoned.

FIELD OF THE INVENTION

The invention relates to the purification of lactoferrin from milk, particularly the purification of human lactoferrin from the milk of transgenic non-human animals expressing a human lactoferrin polypeptide encoded by a transgene.

BACKGROUND

Recent advances in the field of molecular biology allow the production of transgenic animals (i.e., non-human animals containing an exogenous DNA sequence in the genome of germline and somatic cells introduced by way of human intervention). Differences in the regulation of these foreign genes in different cell types make it possible to promote the differential expression of the foreign gene in a preselected tissue, such as the mammary gland, for ease of isolation of the protein encoded by the foreign gene, for a desired activity of the foreign gene product in the selected tissues, or for other reasons.

An advantage of transgenic animals and differential gene expression is the isolation of important proteins in large amounts, especially by economical purification methods. Such proteins are typically exogenous to the transgenic animal and may comprise pharmaceuticals, food additives, nutritional supplements, and the like. However, exogenous proteins are preferably expressed in tissues analogous to those in which they are naturally expressed. For example, exogenous milk proteins (e.g., lactoferrin) are preferably expressed in milk-forming tissues in the transgenic animal. As a result, difficult isolation problems are presented because the exogenous protein is often expressed in the tissue or bodily fluid containing an endogenous counterpart protein (if it exists), and possibly other undesired contaminant species which may have very similar physicochemical properties. Moreover, many exogenous proteins must be substantially purified from other species, frequently purified to homogeneity, prior to their use as pharmaceuticals or food additives.

For example, the production of transgenic bovine species containing a transgene encoding a human lactoferrin polypeptide targeted for expression in mammary secreting cells is described in WO91/08216, incorporated herein by reference. The purification of human lactoferrin (hLF) from a transgenic animal containing a functional endogenous bovine lactoferrin (bLF) gene and a transgene encoding the expression of hLF is complicated by the presence of endogenous bLF which has physicochemical properties similar to human lactoferrin. Even in a transgenic bovine lacking a functional endogenous bLF gene (e.g., as a result of homologous gene targeting to functionally disrupt the endogenous bLF alleles), it is frequently desirable and/or necessary to purify transgene-encoded hLF from other biological macromolecules and contaminant species. Since hLF has potential pharmaceutical uses and may be incorporated in human food products as a nutritive supplement, uses which typically require highly purified hLF, it is imperative that methods be developed to purify hLF from milk, especially from milk or milk fractions of transgenic nonhuman animals such as bovine species.

Human lactoferrin is a single-chain glycoprotein which binds ferric ions. Secreted by exocrine glands (Mason et al. (1978) *J. Clin. Path.* 31: 316; Tennovuo et al. (1986) *Infect. Immunol.* 51: 49) and contained in granules of neutrophilic leukocytes (Mason et al. (1969) *J. Exp. Med.* 130: 643), this protein functions as part of a host nonspecific defense system by inhibiting the growth of a diverse spectrum of bacteria. hLF exhibits a bacteriostatic effect by chelation of the available iron in the medium, making this essential metal inaccessible to the microorganisms (Bullen et al. (1972) *Brit. Med. J.* 1: 69; Griffiths et al. (1977) *Infect. Immunol.* 15: 396; Spik et al. (1978) *Immunology* 8: 663; Stewart et al. (1984) *Int. J. Biochem.* 16: 1043). The bacteriostatic effect may be blocked if ferric ions are present in excess of those needed to saturate the hLF binding sites.

Lactoferrin is a major protein in human milk (present at a concentration of about 1.5–1.7 mg/ml) and may play a role in the absorption of dietary iron by the small intestine. Essentially all of the iron present in human breast milk is reported to be bound to hLF and is taken up at very high efficiency in the intestine as compared to free iron in infant formula (Hide et al. (1981) *Arch. Dis. Child.* 56: 172). It has been postulated that the efficient uptake of hLF-bound iron is due to a receptor in the jejunum. Specific lactoferrin receptors have been reported on mucosal cells of the small intestine of adult humans (Cox et al. (1979) *Biochem. Biophys. Acta* 588: 120).

hLF from human colostrum is available commercially (Calbiochem, La Jolla, Calif. and other vendors) as a lyophilisate for research applications in small amounts (10 mg and 25 mg vials). The amino acid sequence of hLF has been reported (Metz-Boutigue et al. (1984) *Eur. J. Biochem.* 1451: 659), and WO91/08216 reports an hLF sequence having some sequence inconsistencies with the previous report of Metz-Boutigue et al. hLF comprises two domains, each comprising an iron-binding site and an N-linked glycosylation site. These domains show homology with each other, consistent with an ancestral gene duplication and fusion event. hLF also shares extensive sequence homology with other members of the transferrin family (Metz-Boutigue et al. (1984) op.cit.; Pentecost et al. (1987) *J. Biol. Chem.* 262: 10134). A partial cDNA sequence for neutrophil hLF was published by Rado et al. (1987) *Blood* 70: 989), which agrees by more than 98% sequence identity compared to the amino acid sequence determined by direct amino acid sequencing from hLF from human milk. The structures of the iron-saturated and iron-free forms of human lactoferrin have been reported (Anderson et al. (1989) *J. Mol. Biol.* 209: 711; Anderson et al. (1990) *Nature* 344: 784).

Protocols for purifying lactoferrin from milk have been reported. U.S. Pat. No. 4,436,658 describes the isolation of bovine lactoferrin from defatted and casein-free whey of bovine milk. Briefly, whey is contacted with silica in a slightly basic medium at pH 7.7–8.8, the lactoferrin is adsorbed and thereafter eluted with 0.5M NaCl/0.1N acetic acid. U.S. Pat. No. 4,791,193 and European Patent Application No. EP 0 253 395 by Okonogi et al. similarly report a method wherein bovine milk is contacted with carboxymethyl groups of a weakly acidic cation exchange resin and the adsorbed lactoferrin is eluted with a 10 percent NaCl gradient. In U.S. Pat. No. 4,668,771, bLF is isolated from bovine milk using a monoclonal antibody fixed to an insoluble carrier. WO89/04608 describes a process for obtaining fractions of bovine lactoperoxidase and bLF from bovine milk serum; the milk serum is microfiltered and passed through a strong cation exchanger, pH<6.0, at a high rate of flow for selective adsorption of lactoperoxidase and bLF followed by elution with a 0.5–2.0M NaCl solution. U.S. Pat. No. 4,997,914 discloses isolation of hLF from human colostrum or raw milk; the lactoferrin-containing sample is contacted with a sulfuric ester of a crosslinked polysaccharide to bind hLF, followed by elution with a 0.4–1.5 NaCl aqueous solution.

The scientific literature also reports protocols for the isolation of lactoferrin from milk. A number of these involve isolation of LF from a natural source using ion-exchange chromatography followed by salt elution. Querinjean et al. (1971) *Eur. J. Biochem.* 20: 420, report isolation of hLF from human milk on CM Sephadex C-50 followed by elution with 0.33M NaCl. Johannson (1969) *Acta Chem. Scand.* 23: 683 employed CM Sephadex C-50 for purification of LF, and Johannson et al (1958) *Nature* 181: 996 reports the use of calcium phosphate for LF purification. Torres et al. (1979) *Biochem. Biophys. Acta* 576: 385 report lactoferrin isolation from guinea pig milk. The milk was pre-treated by centrifugation to remove fats and to sediment the casein. A Whatman CM-52 column was used, and lactoferrin was eluted with 0.5M NaCl/5 mM sodium phosphate, pH 7.5. Roberts and Boursnell (1975) *Jour. of Reproductive Fertility* 42: 579, report lactoferrin isolated from defatted sow's milk. CM-Sephadex was added to an ammonium ferrous sulfate precipitate of the milk, and the bound lactoferrin was eluted with 0.5M NaCl/20 mM phosphate at pH 7 followed by a second CM-Sephadex fractionation from which the lactoferrin was eluted with 0.4M NaCl. Zagulski et al. (1979) *Prace i Materialy Zootechniczne* 20: 87, report bovine lactoferrin isolated from bovine milk. Defatted bovine milk was mixed with CM-Sephadex C-50, and lactoferrin was eluted from the column with 0.5M sodium chloride/0.02M sodium phosphate at pH 7. Moguilevsky et al. (1975) *Biochem J.* 229: 353, report lactoferrin isolated from human milk, using CM-Sephadex chromatography and elution with 1M sodium chloride. Ekstrand and Bjorck (1986) *Jour. of Chromatography* 358: 429, report lactoferrin isolated from human colostrum and bovine milk. Defatted bovine or human milk was acidified, adjusted to pH 7.8 and applied to a Mono S™ column. The bovine or human lactoferrin was eluted with a continuous salt gradient of 0–1M NaCl. The purification of human lactoferrin from bovine lactoferrin was not reported. Foley and Bates (1987) *Anal. Biochem.* 162: 296, report isolation of lactoferrin from human colostrum whey. The whey was mixed with a weak ion-exchange resin (cellulose phosphate) and proteins were eluted with a stepped salt and pH gradient. Lactoferrin was eluted with 0.25M NaCl/0.2M sodium phosphate at pH 7.5. Further, Yoshida and Ye-Xiuyun (1991) *J. Dairy Sci.* 74: 1439, disclosed the isolation of lactoferrin by ion exchange on carboxymethyl cation resin using 0.05M phosphate buffer at pH 7.7 with a linear gradient of 0–0.55M NaCl. The carboxymethyl-Toyopearl column adsorbed only lactoperoxidase and lactoferrin from the albumin fraction of bovine milk acid whey. Lactoferrin was eluted between 0.4–0.55M NaCl and was separated into two components; lactoferrin A and lactoferrin B.

Other methods, including affinity chromatography, have also been reported. For example, in Kawakami et al. (1987) *J. Dairy Sci.* 70: 752, affinity chromatography of LF with monoclonal antibodies to human or bovine lactoferrin was reported. Human lactoferrin was isolated from human colostrum and bovine lactoferrin from bovine milk or cheese whey. (See also U.S. Pat. No. 4,668,771, cited supra) Hutchens et al. (1989) *Clin. Chem.* 35: 1928, lactoferrin was isolated from the urine of human milk fed preterm infants with single-stranded DNA on an affinity column. Additionally, Chen and Wang (1991) *J. Food Sci.* 56: 701 reported a process combining affinity chromatography with membrane filtration to isolate lactoferrin from bovine cheese whey using heparin-Sepharose to bind lactoferrin. Cheese whey was diluted with a binding buffer and added to the heparin-Sepharose material. The slurry was microfiltered, and the lactoferrin was eluted with 5 mM veronal-hydrochloride/0.6M NaCl at pH 7.4. Bezwoda et al. (1986) *Clin. Chem. Acta* 157: 89 report the use of Cibacron Blue F3GA resin for purification of LF. Ferritin (Pahud et al. (1976) *Protides Biol Fluids.* 23: 571) and heparin (Blackberg (1980) *FEBS Lett.* 109: 180) have also been reported for purification from milk.

Thus there exists a need in the art for methods for purification of human lactoferrin from milk, particularly from milk of nonhuman transgenic animals, such as bovine species, that contain human lactoferrin encoded by a transgene. It is one object of the invention to provide methods and compositions for economical and efficient purification of human lactoferrin from milk, such as bovine milk, for use as a pharmaceutical or food additive. The present invention fulfills these and other needs. It is also an object of the present invention to provide human lactoferrin compositions with a purity of about 98% or greater.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention provides an efficient and effective procedure for purification of human lactoferrin from milk, especially for purification of human lactoferrin from bovine milk produced by transgenic bovine species containing a human lactoferrin transgene. The transgene-encoded human lactoferrin is substantially purified from other milk proteins in the milk of transgenic cows, and is preferably substantially isolated from endogenous bovine lactoferrin, if present in the milk.

The invention provides methods for isolating human lactoferrin, including human lactoferrin produced by expression of a transgene encoding a recombinant human lactoferrin (rhLF), as well as other related lactoferrin species from milk, typically from bovine milk. Such other related lactoferrin species can include truncated hLF, amino acid sequence variants (muteins or polymorphic variants) of hLF, an hLF species which comprises additional residues. The invention also provides methods that permit the purification of human lactoferrin (including rhLF) from bovine lactoferrin, ovine lactoferrin, goat lactoferrin, mouse lactoferrin, and porcine lactoferrin. In general, milk or a milk fraction containing hLF is contacted with a strong cation exchange resin (e.g., S Sepharose™ or Mono S™ sepharose) in the presence of relatively high ionic strength (0.2M to 0.5M NaCl or KCl, preferably 0.4M NaCl or KCl) to prevent binding of non-lactoferrin proteins and other substances to the strong cation exchange resin and to reduce electrostatic interactions of lactoferrin with other proteins (e.g., caseins) or substances (e.g., lipopolysaccharide), and to liberate lactoferrin from complexes. The strong cation exchange resin containing the bound lactoferrin is separated from the unbound compounds in the milk or milk fraction, typically by centrifugation or sedimentation followed by batchwise washing and/or by pouring the resin into a column and washing the beads with buffer having approximately equal or lower salt concentration. The lactoferrin bound to the cation exchange resin is eluted with an aqueous, typically buffered, NaCl or KCl gradient (e.g., linear gradient of 0–1M NaCl in 20 mM sodium phosphate, pH 7.5) or by batch elution or stepwise elution with an aqueous, preferably buffered, NaCl or KCl solution of 0.4M or greater, preferably at least 0.5M NaCl or KCl. By selecting appropriate elution conditions, human lactoferrin may be substantially purified from bovine milk and substantially separated from bovine lactoferrin by an efficient method.

In one aspect of the invention, human lactoferrin (e.g., rhLF) is further purified from endogenous lactoferrin (e.g., bLF) by the additional subsequent step of rechromatography on a strong cation exchanger, such as S Sepharose™ Fast Flow, with salt gradient or stepwise elution to separate human lactoferrin from remaining traces of endogenous nonhuman lactoferrin species (e.g., bLF), and/or may optionally include affinity chromatography with a concanavalin A resin to further separate human lactoferrin from bLF, with bLF being more strongly bound to the Con A resin than hLF.

In a method of the invention, a limiting quantity of a strong cation exchange resin (e.g., an amount less than that needed to saturably bind essentially all of the lactoferrin in the sample) is contacted to milk or a milk fraction (e.g., whey) under aqueous conditions (e.g., by adding resin directly to the milk or milk fraction) whereby the strongest cationic proteins, such as lactoferrin, preferentially and competitively bind to the limiting amount of cation exchange resin present. With a limiting amount of cation exchange resin we thus mean a quantity that is just enough to at least bind essentially all (e.g., 99 percent) of an object lactoferrin species (e.g., human) at a predetermined salt strength of the milk or milk fraction. The amount of strong cation resin to be used is thus limited to optimize the selectivity of lactoferrin binding. The limiting amount of strong cation exchange resin with bound protein is separated from the remainder of the milk or milk fraction, typically by centrifugation or sedimentation followed by batchwise washing and/or pouring the resin into a column followed by columnwise washing of the resin and bound proteins. The lactoferrin bound to the resin is eluted by a high salt buffer (i.e., NaCl or KCl concentration greater than 0.4M) or a salt gradient having a maximal salt concentration of at least about 0.5M NaCl or KCl).

In one variation, an ionic species, such as NaCl or KCl, is added to raw milk, processed milk, or a milk fraction prior to contacting the milk or milk fraction with a strong cation exchange resin. Typically, salt (or a salt solution) is added to the milk or milk fraction to bring the final salt concentration to approximately 0.2M to 0.5M, most preferably to approximately 0.4M in NaCl or KCl, forming a high ionic strength milk solution. The high ionic strength milk solution is contacted with a strong cation exchange resin under binding conditions and the resin containing bound milk protein(s) is separated from the unbound components in the remainder of the high ionic strength milk solution, typically by centrifugation or sedimentation followed by batchwise washing and/or by pouring the strong cation exchange resin mixture into a column and removing the remainder of the high ionic strength milk solution by removing the liquid from the column and/or by washing the resin column with a wash buffer having an approximately equal or lower ionic strength than the high ionic strength milk solution. The lactoferrin bound to the strong cation exchange resin is eluted by a high salt buffer (i.e., NaCl or KCl concentration greater than 0.4M) or a salt gradient having a maximal salt concentration of at least about 0.5M NaCl or KCl). In an optional variation, a detergent, such as a nonionic detergent (e.g., Tween-20) may be added to the milk or milk fraction to reduce undesirable hydrophobic interactions between macromolecules that would reduce the efficiency of lactoferrin purification. The milk or milk fraction also may be substantially diluted, typically to a final salt concentration of about 0.2M to 0.5M NaCl or KCl, preferably 0.4M NaCl or KCl, to further reduce undesired intermolecular interactions that can reduce the yield and/or purity of recovered lactoferrin.

All publications and patent applications herein are incorporated by reference to the same extent as if each individual publication or patent application was specifically and individually indicated to be incorporated by reference.

DEFINITIONS

Figure 1A:
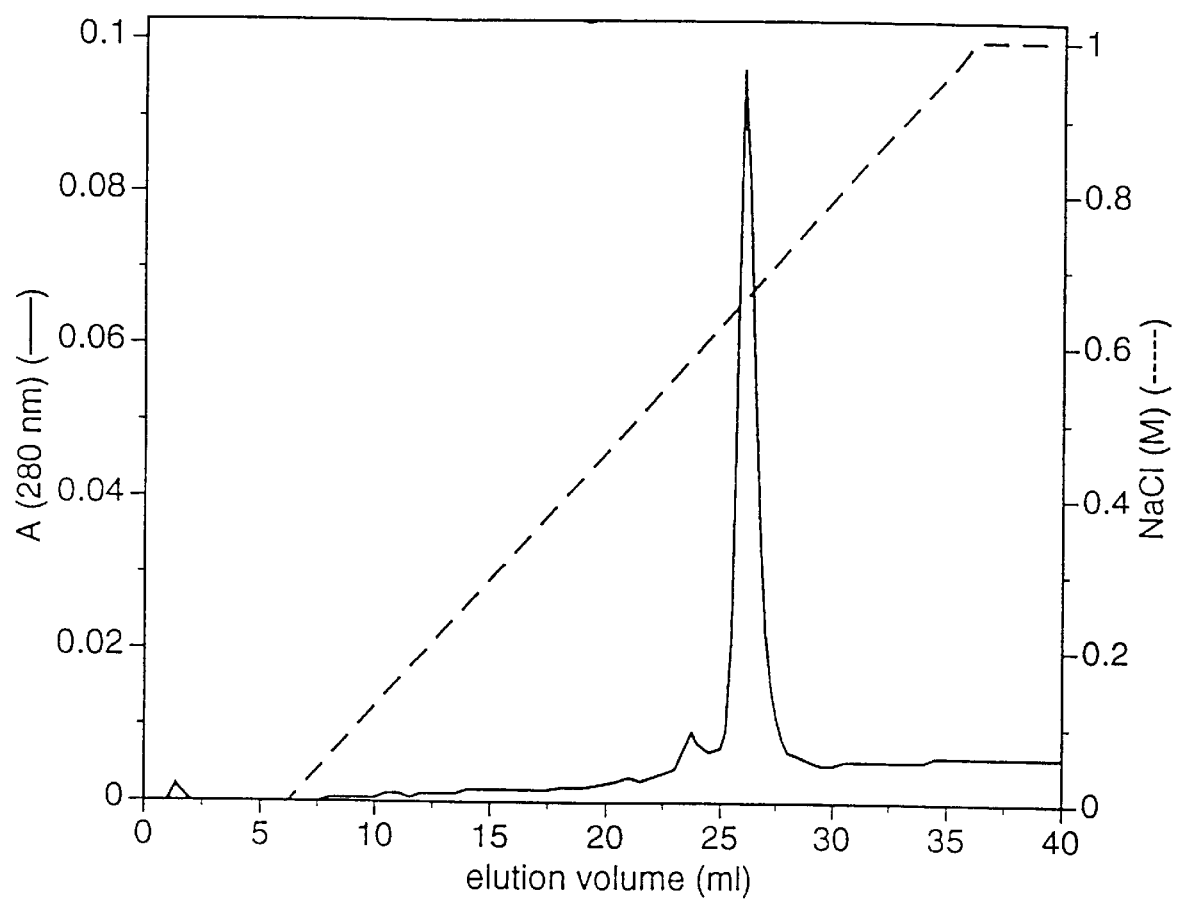
FIG. 1 shows the differential elution profiles of lactoferrin from a strong cation exchange resin, Mono S™ by linear salt gradient. Panel A shows the elution profile of hLF. Panel B shows the elution profile of bLF.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein, the term "enriched" refers to composition or fraction wherein an object species has been partially purified such that, on a molar ratio basis, at least about 10 percent of one or more naturally occurring contaminant species have been removed. For example, a sample from milk of a transgenic bovine expressing human lactoferrin may be enriched for human lactoferrin by selectively removing caseins by acid precipitation (e.g., the whey fraction is thereby enriched for human lactoferrin).

As used herein, "human lactoferrin" comprises a polypeptide having an amino acid sequence substantially as described by Metz-Boutigue et al. (1984) *Eur. J. Biochem.* 1451: 659, noting the sequence inconsistencies identified in PCT publication WO91/08216 and other published protein and DNA sequences. The term human lactoferrin also includes naturally occurring human allelic variants either partially proteolyzed or not ("naturally occuring human lactoferrin") and amino acid sequence variants that have been modified by the insertion, substitution, or deletion of one or more amino acids as compared to a naturally occurring human lactoferrin species and which have a greater degree of sequence identity when optimally aligned (and gapped, if necessary) to a naturally occurring human lactoferrin amino acid sequence of at least 50 contiguous amino acids than to other naturally occurring polypeptide species of at least contiguous 50 amino acids. Human lactoferrin also includes recombinantly encoded human lactoferrin ("rhLF") expressed in a transgenic nonhuman animal, such as a bovine, where the glycosylation pattern may be distinct from glycosylation patterns on naturally occuring human lactoferrin obtained from human milk.

DETAILED DESCRIPTION

Human lactoferrin may be used for pharmaceutical uses (WO91/13629, incorporated herein by reference), as a nutrient supplement, and for other uses. For such uses it is frequently necessary or preferable to employ human lactoferrin which has been purified, either partially or essentially to homogeneity, from undesired contaminants in milk, especially from other milk proteins (e.g., whey proteins, caseins), milk fat, and other contaminants (e.g., lipopolysaccharide of Gram-negative bacteria) present in milk samples. Lactoferrins have been reported to interact with a wide variety of milk proteins including IgA, caseins, SC, albumin, lysozyme, β-lactoglobulin, and others. The present invention provides purification methods which advantageously afford the efficient and rapid purification of lactoferrin, especially human lactoferrin, from milk, such as milk produced by transgenic bovine species harboring a human lactoferrin transgene which is expressed in the mammary gland.

A basis of the invention is the finding that lactoferrin, especially human lactoferrin, has a surprisingly strong affinity for strong cation exchange resins which can be exploited to purify lactoferrin from milk, especially to purify human lactoferrin from milk of transgenic bovine species expressing a human lactoferrin transgene. It has also been discovered that elevating the ionic strength of milk or a milk fraction to approximately 0.2–0.5M NaCl or KCl or equivalent salt, preferably approximately 0.35–0.4M NaCl or KCl, more preferably approximately 0.4M NaCl or KCl, and typically 0.4M NaCl concomitant with contacting the milk or milk fraction with the strong cation exchange resin(s) enhances recovery and resolution of lactoferrin from undesired contaminants in the milk or milk fraction. The addition of relatively high salt conditions (e.g., to a final concentration of about 0.4M NaCl) to milk or milk fractions strongly reduces binding of most contaminant proteins (e.g., whey proteins and caseins) and lipopolysaccharides ("LPS") to a strong cation exchange resin (e.g., Mono S™ or S Sepharose™ Fast Flow) while permitting efficient binding of lactoferrin (e.g., rhLF) to the strong cation exchange resin, thus providing a convenient basis for separation of lactoferrin from contaminant molecular species. It is noted that elevating the ionic strength of milk or milk fractions to approximately 0.35–0.4 M NaCl virtually excludes the binding of any other bovine milk protein other than lactoferrin to a strong cation exchange resin. The elution profile of bovine whey that has been applied to Mono S™ under conditions of low ionic strength shows that all bound bovine whey proteins (except lactoferrin) elute at NaCl concnetrations of 0.3 M NaCl (e.g., bovine lactoperoxidase) or lower (other proteins). Moreover, it has also been found that strong cation exchange resins and relatively high salt conditions may be used to separate human lactoferrin from bovine lactoferrin in milk or milk fractions. Elevated salt conditions (NaCl concentration at least 10 mM greater than physiological milk, i.e., milk or milk fraction used as a staring material for the purification of LF, generally 0.2M NaCl or greater) are used to enhance specific loading of human lactoferrin onto strong cation exchange resins. Elevated ionic strength milk or milk fractions exhibit more selective binding of hLF to the strong cation exchange resin selected.

In a preferred embodiment, human lactoferrin is expressed and secreted into the milk of a transgenic animal, preferably a bovine species. In those embodiments where rhLF is expressed and secreted into the milk of transgenic bovine species, the transgenic milk may be either used as obtained or further treated to purify the rhLF. The human lactoferrin obtained by the methods of the invention preferably is obtained by processing a milk fraction, although raw milk (whole milk) may also be used. Preferable milk fractions include defatted milk, defatted milk from which particulate matter and/or caseins have been removed (e.g., milk whey), and other milk fractions which contain lactoferrin.

Preparation of Milk and Milk Fractions

Raw milk is harvested from the transgenic nonhuman animal expressing human lactoferrin. The raw milk (whole milk) may optionally be adjusted to a relatively high ionic strength (e.g., 0.3–0.4M NaCl or KCl) by addition of solid NaCl, KCl, or other suitable salt, or an aqueous solution thereof. Combinations of monovalent salts may be used (e.g., NaCl and KCl together), if desired, so that the final concentration of monovalent cation in the milk will be approximately 0.3–0.4M. The whole milk may be contacted with a strong cation exchange resin directly, or may be processed into a milk fraction which is subsequently contacted with a strong cation exchange resin under conditions of relatively high ionic strength (e.g., 0.3–0.4M NaCl or KCl). If the whole milk is to be contacted with a strong cation exchange resin directly, the ionic strength is adjusted by increasing the salt concentration in the whole milk, typically to approximately 0.35–0.4M NaCl or KCl, prior to or concomitant with contacting the whole milk with the strong cation exchange resin. Optionally, the whole milk may be diluted with an aqueous solution, typically a buffered salt solution, to produce diluted whole milk having a monovalent cation (e.g., $Na^+$, $K^+$, or combination thereof) concentration of approximately 0.3–0.4M. Usually a buffered salt solution used as a whole milk diluent will have a NaCl (or KCl) concentration of at least about 0.3–0.4M and will be buffered to pH 6–8 with a suitable buffer; the final concentration of monovalent cation(s) in the diluted milk is preferably 0.3–0.4M, more preferably 0.4M, and thus cationic species contributed by a buffer, such as a sodium phosphate buffer, should be taken into account along with the dissolved salt species (e.g., NaCl and KCl). Thus, high ionic strength milk (i.e., milk having at least approximately 0.3–0.4M monovalent cation) may be generated by either adding and dissolving one or more solid salts (e.g. NaCl or KCl) in whole milk or by diluting whole milk in a diluent salt solution whereby the final concentration of monovalent cation in the diluted milk is approximately 0.3–0.4M. High ionic strength whole milk (diluted or undiluted) may be used directly for contacting with a strong cation exchange resin, or may be processed further into a milk fraction prior to contacting with a strong cation exchange resin. Whole milk which has not had the ionic strength increased by the addition of salt typically is processed into a milk fraction, the ionic strength of the milk fraction is then increased by addition of one or more salts to increase the concentration of monovalent cation to approximately 0.3–0.4M, and the high ionic strength milk fraction is contacted with a strong cation exchange resin.

Without wishing to be bound by any particular theory, dilution of whole milk may also decrease undesired intermolecular interactions between lactoferrin (e.g., rhLF) and contaminant macromolecular species (e.g., caseins, LPS of Gram-negative bacteria) present in milk. However, significant dilution of whole milk or milk fractions may result in large volumes which may be less efficiently processed. It has been found that increasing the ionic strength of the milk also substantially decreases undesired intermolecular interactions between lactoferrin (e.g., rhLF) and contaminant macromolecular species, permitting a more facile purification without necessitating dilution of milk to large volumes, unless desired. Optionally, addition of a non-interfering detergent (i.e., does not substantially reduce binding of hLF to resin), such as a nonionic surfactant (e.g., Tween-20), to a concentration of approximately 0.001–0.2 percent, preferably about 0.01–0.03 percent, may also contribute to reducing undesired intermolecular interactions involving lactoferrin.

Processing of whole milk, either directly or after increasing the ionic strength by addition of salt (e.g., NaCl or KCl), into a milk fraction containing lactoferrin prior to contacting with a strong cation exchange resin may further reduce the amount of one or more contaminant species. For example, defatting of whole milk can remove a significant proportion of lipid species which may be undesirable and which may interfere with efficient purification of lactoferrin by strong cation exchange chromatography.

The human lactoferrin obtained by the process of the invention is preferably obtained by processing transgenic milk whey. Milk whey is a milk fraction produced by removing substantially all fats and caseins from the transgenic milk. A variety of methods (e.g., centrifugation) are known to those skilled in the art to remove fats from milk. Similarly, a number of procedures are known to those skilled in the art for removal of caseins from milk. For example, acid precipitation or proteolysis of kappa-casein by chymosin may be used to remove casein from milk. Other compatible methods for generating milk fractions containing lactoferrin (e.g., whey) known to those skilled in the art may be used. Although salt may be added subsequent to the removal of caseins from the milk, that order of addition may result in the loss of significant amounts of lactoferrin, as caseins are generally highly phosphorylated (i.e., negatively charged) and may bind substantial amounts of lactoferrin, presumably by electrostatic interactions; thus, removal of caseins from milk under low salt conditions may result in the undesirable removal of substantial amounts of lactoferrin as well.

In a preferred embodiment, salt (e.g., NaCl or KCl) is added to whole milk of a transgenic nonhuman animal expressing human lactoferrin before defatting and removal of caseins; alternatively, salt may be added after defatting but prior to removal of caseins. Typically, an aqueous solution containing NaCl and a sodium phosphate buffer is used to dilute whole milk to form high ionic strength milk having a final concentration of 10–50 mM sodium phosphate, 0.3–0.4M NaCl at about pH 6.5–7.5. The high ionic strength milk typically has a final concentration of 20 mM sodium phosphate, 0.4M NaCl at about pH 7.0. Optionally, a surfactant may be included to a final concentration of about 0.001–0.2 percent by volume, with a typical concentration being approximately 0.02 percent v/v. Usually, a nonionic surfactant such as Tween-20 is used, other nonionic surfactants may also be suitable. Thus, in this embodiment, defatted milk containing approximately 0.4 M NaCl, and optionally containing about 0.02 percent Tween 20, is produced and subsequently used for removal of caseins by conventional methods to produce a high ionic strength whey containing lactoferrin. After the foregoing step, the high ionic strength whey is contacted with a strong cation exchange resin (e.g., S Sepharose™ Fast Flow, Pharmacia Biotechnology, Piscataway, N.J.) under suitable binding conditions whereby the strong cation exchange resin preferentially binds lactoferrin from the high ionic strength whey to produce a lactoferrin-resin complex.

Binding of Lactoferrin to Strong Cation Exchange Resins

Human lactoferrin (calculated pI approximately 8.5) essentially does not bind to the strong anion exchange resin Mono Q™ at pH 4.5 and weakly binds at pH 7.5 (i.e., even at pH values below its pI), which is consistent with the idea that charge is unevenly distributed over the surface of the human lactoferrin molecule.

However, human lactoferrin binds essentially completely to strong cation exchange resins, such as Mono S™ or S Sepharose™, between approximately pH 4.5 and 9.5 and at monovalent cation concentrations equivalent to approximately 0.5M NaCl or less, preferably 0.45M NaCl or less. This finding is consistent with a hypothesis that human lactoferrin behaves as a molecular dipole, possibly with the many basic amino acids (Arg and Lys) clustered together in the amino-terminal portion. This finding provides a basis for purification of human lactoferrin from milk by reversible adsorption to a strong cation exchange resin under conditions of relatively high salt.

A multitude of strong cation exchange resins are known to those of skill in the art of protein purification. "Strong cation exchange resins" are defined as those which exchange their diffusible cation only under conditions of high ionic strength, such as those containing sulfite or sulphate groups. Presently preferred strong cation exchange resins are, for example, Mono S™ cation exchange resin and S Sepharose™ Fast Flow cation exchange resin (available from Pharmacia/Pharmacia LKB Biotechnology, Piscataway, N.J.). The Mono S™ and S Sepharose™ Fast Flow cation exchange resins currently use ligand S, although ligand SP is suitable as well and may be substituted. Resins with similarly charged groups providing strong cation exchange will also be useful for purposes of the invention.

A variety of methods may be used to contact the milk or milk fraction, including transgenic bovine whey containing human lactoferrin with a strong cation exchange resin. For example, the strong cation exchange resin may be formed into a column and the lactoferrin-containing whey may be passed through the column. After adsorption of the lactoferrin to the column resin, the column is washed and the human lactoferrin is subsequently desorbed by elution at an ionic strength sufficient to elute the human lactoferrin, preferably at an ionic strength sufficient to elute human lactoferrin efficiently but not substantially elute bovine lactoferrin, if present. Alternatively, the lactoferrin-containing whey may be contacted with a strong cation exchange resin in the form of a bed, generally under conditions of relatively high ionic strength (e.g., 0.35–0.4M NaCl, pH 7.0). In this case, the lactoferrin-containing whey is contacted with the strong cation exchange resin in a bed and agitated for a suitable period of time at a suitable temperature (e.g., 4–30 degrees Celsius); such contacting may be accomplished by mixing resin beads directly into the lactoferrin-containing whey. Subsequently, the strong cation exchange resin with the adsorbed lactoferrin is separated by, for example, centrifugation, spontaneous sedimentation, or by being formed into a column, and the mobile phase (i.e., lactoferrin-depleted whey) substantially removed.

The isolated lactoferrin-resin complexes can be washed to remove remaining unbound or resin-bound non-lactoferrin species, if desired, with a wash buffer having an ionic strength sufficiently low (e.g., monovalent cation concentration less than about 0.45M) to prevent substantial elution of lactoferrin from the resin, but preferably sufficiently high to elute non-lactoferrin macromolecules which may or may not be bound to the resin. Typically, a wash buffer can comprise between about 0.01–0.45M NaCl, 5–50 mM sodium phosphate buffer at approximately pH 7.5, although other wash solutions may be used. For example, a wash buffer containing 0.3M NaCl, 10 mM sodium phosphate pH 7.5 may be used. Optionally, a detergent such as a nonionic surfactant (e.g., Tween-20) may be included in a wash buffer, typically at 0.01–0.1 percent by volume. The isolated lactoferrin-resin complexes may be washed in a single washing step, in multiple washing steps, or may remain unwashed. Generally, at least one volume of wash buffer per unit volume of resin is used to wash the isolated lactoferrin-resin complexes, frequently larger wash volumes are used, especially if the wash buffer has low ionic strength (e.g., less than 0.2 M NaCl), if washing is performed. Washing serves to remove non-lactoferrin macromolecules from the resin whether in column or bed form.

Lactoferrin is selectively desorbed from the isolated lactoferrin-resin complexes by elution with a solution of appropriate ionic strength. Generally, an elution buffer will comprise a monovalent salt (e.g., NaCl or KCl) at a concentration of at least approximately 0.3–0.4M, typically 0.45–0.5M or greater, and preferably also contains a suitable buffer, such as sodium phosphate (e.g., 5–50 mM) at a pH of approximately 7.5. A variety of salt concentrations and compositions of the elution solution are possible, and may vary with the scale of purification, so that calibration or standardization of column or resin bed performance may be performed by those skilled in the art using standard calibration methods. Alternatively, human lactoferrin can be selectively desorbed from the lactoferrin-resin complexes packed in a column by elution with an NaCl or KCl gradient or step gradient as the mobile phase, with desorption of human lactoferrin typically occurring at approximately 0.30–0.75M NaCl, depending upon the scale of purification and other column performance factors. Calibration of column performance and determination of elution profile can be readily determined by those of skill in the art for each embodiment. The fraction(s) containing human lactoferrin may be identified by any convenient assay for human lactoferrin, including but not limited to: immunoassay using antibody which specifically binds human lactoferrin (Nuijens et al. (1992) *J. Lab. Clin. Med.* 119: 159) or other assays for detecting and quantitating lactoferrin.

In a further embodiment, lactoferrin is removed from lactoferrin-resin complexes by dialysis. Dialysis is a widely practiced technique known to those of skill in the art. The dialysis membrane is selected such that the protein, for example human lactoferrin, passes unimpeded from one side of the membrane to the other. In the present case, a strong cation exchange resin is present on the side of the membrane opposite the side contacting the transgenic milk or milk fraction containing lactoferrin. Lactoferrins, including human and bovine lactoferrin, partition from the milk or milk fraction across the dialysis membrane to the side containing the strong cation exchange resin, where they bind the strong cation exchange resin. The pore size (molecular weight cutoff) of the dialysis membrane selected prevents the lactoferrin-resin complexes from passing across the membrane into the milk or milk fraction. In this embodiment, the dialysis membrane is selected so that only the unbound lactoferrin, and not the lactoferrin bound to the strong cation exchange resin, passes across the membrane. Typically, the milk or milk fraction is adjusted to an ionic strength of about 0.35–0.4M monovalent salt (NaCl or KCl) and is generally buffered to a pH of about 7.5, usually with a suitable buffer (e.g., sodium phosphate, potassium phosphate) prior to or concomitant to contacting the milk or milk fraction with the dialysis membrane separating the strong cation exchange resin from the milk or milk fraction. Optionally, a detergent, such as a nonionic surfactant (e.g., Tween-20), may be included at a concentration of approximately 0.001 to 0.2 percent v/v, preferably about 0.02 percent v/v, if present. After a suitable dialysis period for allowing partition of lactoferrin across the membrane to bind to the strong cation exchange resin, the milk or milk fraction thus depleted of lactoferrin is removed and the lactoferrin bound to the strong cation exchange resin is eluted, either directly or across a dialysis membrane, by contacting the lactoferrin-resin complexes with a high ionic strength buffer (e.g., 0.45–0.7M NaCl or KCl, 5–50 mM sodium phosphate or potassium phosphate pH 7.5). A variety of alternate aqueous solutions may be used to elute the lactoferrin from the strong cation exchange resin and will be apparent to those of skill in the art. Substitution of other salts (e.g., LiCl), including salts of divalent cations may also be employed by those of skill in the art to practice the invention.

Lactoferrin eluted from the lactoferrin-resin complexes may be subjected to an additional round of cation exchange chromatography and/or lectin (e.g., Con A) affinity chromatography to resolve further the human lactoferrin from bovine lactoferrin, if present. Moreover, rechromatography may be used to purify further intact human lactoferrin from degradation (proteolyzed) products. Preferably, intact human lactoferrin is recovered in substantially pure form.

After eluting the lactoferrin from the bound lactoferrin-resin complexes with a high ionic strength salt solution, the eluted lactoferrin may be treated to clarify and concentrate it. Preferably the recovered lactoferrin is dialyzed to remove salts, ultrafiltered, and optionally lyophilized to concentrate the lactoferrin. Suitable storage and/or reconstitution components (e.g., buffers, salts, preservatives, antibiologicals, ferric ions) may be added to the purified lactoferrin.

Purification of Lactoferrin from Milk by Batch Extraction

Batch extraction of lactoferrin from milk using a strong cation exchange resin is believed to be a preferred purification strategy for large scale industrial applications.

In batch extraction, it is generally preferable that salt is added to the milk or milk fraction to produce a high ionic strength milk solution (e.g., 0.4M NaCl) prior to, or concomitant with, contacting the strong cation exchange resin with the milk solution. It is believed that salt is added to increase the ionic strength sufficiently to (1) reduce potential intermolecular electrostatic interactions between contaminants (e.g., caseins and LPS) and lactoferrin, (2) reduce binding of non-lactoferrin macromolecules to the strong cation exchange resin, i.e., to secure selectivity of lactoferrin binding in case a non-limiting amount of a strong cation exchange resin (protein-binding capacity in excess of the amount of object lactoferrin species) is added to milk or milk fraction, (3) induce aggregation of certain non-lactoferrin species which may then be removed before a column is prepared, and (4) prevent aggregation of materials (possibly including lactoferrin) that may be retained on the resin in low salt conditions and become captured in the chromatography column when a high ionic strength wash or salt gradient is applied, thus impeding column performance and allowing partial disaggregation and elution of the aggregate to contaminate eluted lactoferrin. However, the ionic strength should not be excessively high so that lactoferrin is not efficiently bound by the strong cation exchange resin. For example, an ionic strength of approximately 0.35–0.45M NaCl is generally preferred, with 0.4M NaCl typically used.

Further, when lactoferrin is extracted from milk fractions such as whey (e.g., prepared by acid precipitation, chymosin treatment, or ultracentrifugation), the recovery of lactoferrin is increased if salt has been added to increase the ionic strength prior to casein removal. This effect is presumably due to the trapping of lactoferrin by electrostatic interaction with caseins and may be overcome by increasing the ionic strength prior to casein removal.

For example and not limitation, milk from a transgenic nonhuman animal expressing rhLF may be processed according to the following protocol for substantially purifying the human lactoferrin from the milk.

First, solid NaCl or a 5M NaCl stock solution is added to the milk to produce a final concentration of 0.35–0.45M NaCl, usually about 0.4M NaCl. optionally, a nonionic surfactant (Tween-20) is added up to a 0.02 percent (v/v) final concentration. Sodium phosphate is optionally added to a final concentration of about 20 mM with an expected pH of about 7.5, for example by adding $NaH_2PO_4 \cdot H_2O$ and $Na_2HPO_4 \cdot 2H_2O$ up to a final concentration of 3.2 mM and 16.8 mM, respectively; the final pH of the milk solution need not be exactly 7.5, and frequently will be approximately 6.5–7.0. It is believed that the addition of sodium phosphate (or other buffering agent) may be omitted, as hLF binds efficiently to strong cation exchange resins (e.g., Mono-S™ or S Sepharose™) at pH values between 4.5 and 9.5. Milk fat is removed by centrifugation at 1600×g for 10 minutes in 500 ml polyallomer tubes in a Beckman JA-10 rotor to produce high ionic strength skim milk. Alternatively, spontaneous sedimentation followed by physical removal of the fat layer may be used. Alternatively, milk fat may be removed by centrifugation after batchwise incubation of processed milk with a strong cation exchange resin. A strong cation exchange resin (e.g., S Sepharose™, Pharmacia LKB, Piscataway, N.J.) ) typically is equilibrated with high ionic strength buffer (0.4M NaCl, 20 mM sodium phosphate, pH 7.5, optionally including 0.02 percent Tween-20) and dissolved in the processed milk. Approximately 1 ml of packed, equilibrated strong cation exchange resin beads equilibrated with high ionic strength buffer are added per 5–20 mg of lactoferrin in the processed milk sample (which may be determined by lactoferrin assay) and stirred for a suitable mixing period (e.g., about 1 hour or more, preferably overnight) to bind the lactoferrin to the resin beads. The resin beads (e.g., Fast-S™) are then pelleted by centrifugation at approximately 1600×g for 5 minutes and the supernatant is removed. Alternatively, beads may be pelleted by spontaneous sedimentation after which either high ionic strength skimmed or whole milk depleted of lactoferrin is removed. The pelleted resin beads are washed three times with approximately one volume of high ionic strength buffer, and the resin beads with one volume of washing buffer are then poured into a column. A substantially purified preparation of lactoferrin is eluted from the column with a gradient (i.e., 1.25 times the column volume) of 0.4–1.0M NaCl in 20 mM sodium phosphate pH 7.5. Excess salt present in the recovered lactoferrin can be removed by dialysis against saline or phosphate buffered saline (dialysis against distilled water tends to cause precipitation of lactoferrin). Human lactoferrin can be separated from endogenous (nonhuman; e.g., bovine) lactoferrin by eluting the column with a salt gradient or stepwise elution, with native human lactoferrin (e.g., rhLF) eluting from the column at a lower ionic strength than nonhuman lactoferrin at pH 9.5 or lower. For example, when using a buffer of 20 mM sodium phosphate pH 7.5, rhLF typically elutes at a NaCl concentration that is approximately 50–100 mM (typically 70 mM) lower than the NaCl concentration at which efficient elution of bLF occurs. If additional purification of rhLF from bLF is desired, the recovered fractions containing substantial amounts of rhLF may be rechromatographed on a strong cation exchange resin and/or ConA column and eluted with a salt gradient or stepwise elution to resolve further the hLF from bLF in the eluted fractions.

Lactoferrin Formulations

Lactoferrin produced by the methods of the invention is substantially purified. That is, the lactoferrin is substantially free from contamination with other milk proteins and molecular contaminants present in milk, including bacterial lipopolysaccharides. Human lactoferrin produced by the methods of the invention is suitable for formulation in pharmaceutical or nutrient supplements comprising lactoferrin, typically comprising from at least about 1 milligram to several grams or more of lactoferrin per dose. In view of the antibacterial and anti-inflammatory properties of human lactoferrin, a variety of uses for the purified human lactoferrin are possible. For example, antibacterial pharmaceuticals and/or nutritional supplements comprising lactoferrin, especially human lactoferrin, may be produced and administered, typically in conjunction with other agents, to a patient for therapy or prophylaxis of local infection, large scale (bacterial) infection, blood-borne infection (sepsis) as well as inflammation resulting from an infection or non-infectious inflammatory diseases (e.g., chronic inflammatory disease of ileum or colon). Such pharmaceutical compositions are prepared containing lactoferrin, preferably human lactoferrin, in combination with a physiologically compatible carrier, typically for administration as an aqueous solution (e.g., in physiological saline) by intravenous, intramuscular, subcutaneous, topical, gavage, lavage, or other suitable routes of administration.

Similarly, pharmaceutical preparations and nutritionals containing substantially purified lactoferrin can be used, typically in conjunction with other pharmaceuticals or nutritionals, to treat large scale bacterial infections. For example, pharmaceutical preparations containing human lactoferrin can be used to treat blood-borne bacterial infections, either alone or in conjunction with another pharmaceutical agent, or are used to prepare or treat organ transplant recipients or other immunosuppressed individuals (e.g., AIDS patients) against the effects of infections.

Additionally, the substantially purified human lactoferrin can be used in the formulation of nutritional supplements. For example, for human use, the purified human lactoferrin can be included in infant formulas or be used as an adult dietary supplement. As a result of lactoferrin's iron-binding properties, nutritional preparations useful for treating iron deficiencies (e.g., iron deficiency anemia or premature infants) may be formulated with substantially purified lactoferrin.

Quality Control Assays for Lactoferrin

Quality control of purified hLF should include at least one, preferably more, optionally all of the following procedures: (1) non-reduced and reduced SDS-PAGE, with samples loaded without prior boiling and after boiling, (2) spectroscopic analysis such as absorption measurement at 280 and 465 nm, (3) radioimmunoassay analysis of hLF and bLF, (4) strong cation exchange chromatography (e.g., Mono S™), and (5) N-terminal protein sequencing.

The following examples are offered for illustration and not to limit the invention.

EXPERIMENTAL EXAMPLES

Effect of ionic strength on lactoferrin recovery

We have found that the addition of salt to transgenic mouse and bovine milk before caseins are removed very significantly increases the yield of transgenic hLF and bLF, respectively, upon purification from whey fraction. The data presented in Table 1 provide the background for these differential recoveries.

TABLE 1

| | % of total bLF | | |
|---|---|---|---|
| | only centrifugation | | acid precipitation/ centrifugation |
| Samples | no addition | +0.4 M NaCl | no addition |
| Whole cow milk | 100 + 13 | 100 + 13 | 100 + 11 |
| Casein fraction | 21 + 6[a] | 4 + 3 | 32 + 10[b] |
| Whey fraction | 83 + 6 | 99 + 11 | 72 + 10 | bLF was determined by competitive inhibition RIA in samples of whole bovine milk (n=10) as well as in whey and casein fractions prepared after centrifugation for 30 min at 10,000 g. Acid precipitation was performed by adjusting whole milk to pH 4.6, followed by incubating the milk for 30 min at 40° C. Results (mean+SD) are expressed as percentage of total bLF found in respective fractions.
[a]-bLF concentration in the casein pellets was on the average 4.0 times higher than in the whey fraction. [b]-bLF concentration in the casein pellets was on the average 8.0 times higher than in the whey fraction.

Effect of Ionic Strength and Detergent on Human Lactoferrin Binding

The effects of salt concentration and the presence of nonionic surfactant (Tween-20) or cationic surfactant (Polybrene) on binding of human lactoferrin (hLF) labeled with $^{125}$I to various ligands immobilized on Sepharose were determined. Sepharoses were suspended in 10 mM sodium phosphate, 0.15 NaCl, pH 7.4. The following ligands were immobilized on Sepharose and used for determination of binding to hLF: R595, an LPS from *S. Minnesota* (KDO$^+$, no O antigen, rough); J5, an LPS from *E. coli* (KDO$^+$, no O antigen, rough); heparin, a polyanion known to bind lactoferrin; HSA, human serum albumin; and glycine. $^{125}$I labelled hLF was contacted with the Sepharose-ligand resins and exposed to various combinations of NaCl concentration and detergent. Table 2 shows the percentage of $^{125}$I-hLF (i.e., radioactivity) retained on the various Sepharose-ligand resins.

TABLE 2

Binding of $^{125}$-I-HLF

| | Ligand Immobilized on Sepharose | | | | |
|---|---|---|---|---|---|
| Addition | R595 | J5 | Glycine | Heparin | HSA |
| no | 68 | 57 | 5 | 68 | 8 |
| +0.2% Tw | 70 | 57 | 5 | 65 | 9 |
| +0.2% Tw +0.25 M NaCL | 10 | 7 | 3 | 35 | 4 |
| +0.2% Tw +0.5 M NaCL | 5 | 5 | 2 | 5 | 3 |
| +0.2% Tw +1 M NaCL | 4 | 4 | 1 | 2 | 2 |
| +0.2% Tw +2 M NaCL | 3 | 4 | 1 | 3 | 4 |
| +0.2% Tw +0.1% Polybrene | 18 | 13 | 3 | 6 | 4 |

Table 2 indicates that ionic strength of greater than about 0.4M NaCl and detergent concentration of 0.2% Tween-20 substantially reduces binding of hLF to various ligand species, including bacterial LPS. This experiment indicates that the interaction between LPS and hLF is of electrostatic nature.

Studies were performed to determine the binding of hLF to LPS types from a wide variety (i.e., more than 50 types) of clinically relevant Gram-negative bacteria. Lactoferrin reacted with varying affinities to each type of LPS evaluated. Lactoferrin appeared to electrostatically interact wit the lipid A moiety of LPS, to a site identical or in close proximity to the site of interaction of LPS with Polymyxin B, an antibiotic known to neutralize the toxic effects of LPS.

Elution Pattern of Lactoferrin from Ion Exchange Resins

Fifty micrograms of protein (hLF Sigma 1—see legend of Table 5—and bLF, Sigma, St. Louis, Mo.) in various buffered solutions of different pH was applied to Pharmacia HR5/5 columns containing 1 ml of Mono S™ (strong cation exchanger) or Mono Q™ (strong anion exchanger) resin equilibrated in appropriate buffers using the FPLC™ system (Pharmacia, Piscataway, N.J.) for determination of elution profiles with NaCl in various buffers of various pH (sodium succinate, sodium acetate, sodium phosphate, Hepes, Tris, ethanolamine, N-methylpiperidine). After washing each column with 2 ml of the buffer, a linear salt gradient from 0–1.0M NaCl in 30 ml of buffer was applied at a flow rate of 1 ml/min. Peaks were monitored by absorption measurement at 280 nm. The elution of hLF and bLF in various buffer systems are shown in Table 3.

TABLE 3

Elution pattern of LF preparations on Mono S ™ and MonoQ ™ columns

| Sample (FPLC run no.) | Buffer | NaCl concentration (M) at which a peak is eluted. (% of total hLF eluting at this position) | | |
|---|---|---|---|---|
| | | Mono S ™ | | |
| hLF(330) | 50 mM Na succ pH 4.5 | 0.56(18.2) | 0.63(44.3) | 0.69(37.1) |
| hLF(311) | 50 mM Na acet pH 5.0 | 0.57(18) | 0.65(42.4) | 0.72(38.4) |
| hLF(309) | 20 mM Na phos pH 7.5 | 0.51(20.1) | 0.59(46.3) | 0.68(33.8) |
| hLF(306) | 50 mM Hepes pH 7.5 | 0.51(21.5) | 0.60(43) | 0.69(34.7) |
| hLF(352) | 20 mM Tri pH 7.5 | 0.53(9.4) | 0.53(48.2) | 0.71(16.5) |
| hLF(278) | 20 mM Tris pH 7.5 | 0.52(23.2) | 0.61(50.8) | 0.71(25.5) |
| bLF(280) | 20 mM Tris pH 7.5 | | | 0.78(100) |
| hLF(355)[b] | 50 mM Hepes pH 8.0 | 0.45(23.1) | 0.53(42.3) | 0.64(20.1) |
| hLF(350)[a] | 20 mM eth am pH 9.5 | 0.43(23.5) | 0.51(39.5) | 0.60(15) |
| | | | | Mono Q |
| hLF(368) | 20 mM N-meth pip pH 4.5 | no binding | | |
| hLF(360) | 20 mM Tris pH 7.5 | 0.11 | | |
| bLF(363) | 20 mM Tris pH 7.5 | 0–0.23 | | |
| hLF(365) | 20 mM eth am pH 9.5 | 0.16 | | |

[a]about 21% of the hLF applied did not bind to the column.
[b]about 14% of the hLF applied did not bind to the column.

Table 3 shows that hLF binds completely to Mono S™ between pH 4.5 and 9.5, indicating that basic amino acid residues are clustered in hLF. Indeed, the N-terminus of hLF contains clustered basic amino acid residues and thus hLF appears as a macromolecular dipole. hLF elutes in three peaks, in contrast to the literature data. Reduced and non-reduced SDS-PAGE analysis of hLF peaks I, II, and III (see Tables 2 and 4) revealed no cleavage of hLF. All peaks contained the same proportion of Fe-hLF (non-reduced, nonboiled SDS-PAGE). The amount of hLF detected by RIA corresponds to the chromatogram.

hLF does not bind to Mono Q™ at pH 4.5 and binds weakly at pH 7.5 (pH value below its pI). This correlates with the idea that charge is unevenly distributed over the hLF molecule. On the basis of these findings, we selected a strong cation exchange resin at approximately neutral pH for purification of hLF.

Batch Purification of Lactoferrin from Milk

Lactoferrins were purified from human milk, bovine milk, and milk from transgenic mice expressing rhLF in their milk by the batch extraction method. Solid NaCl was added to a final concentration of 0.4M and Tween-20 was added to a final concentration of 0.02% (v/v). Sodium phosphate buffer (pH 7.5) was added to 20 mM final concentration but final pH was not adjusted to 7.5. Milk fat was removed by centrifugation for 10 minutes at 1600×g in 500 ml polyallomer tubes in a Beckman JA-10 rotor. Packed S Sepharose™ Fast Flow equilibrated with starting buffer (0.4M NaCl, 20 mM sodium phosphate, pH 7.5, 0.02% Tween-20) was added to the processed milk at a ratio of approximately 1 ml of packed resin beads per 5–10 mg of lactoferrin in the processed milk. The mixture was stirred for 20 hours, and the resin beads were isolated by centrifugation at 1600×g for 5 minutes. Supernatant was removed and the beads were washed three times with one volume of starting buffer. The resin was then poured into a column and washed with one volume of 20 mM sodium phosphate, 0.4 M NaCl, pH 7.5. Lactoferrin is eluted from the column with a gradient of 0.4–1.0M NaCl in 1.25 (times the column) volume of 20 mM sodium phosphate, pH 7.5, with a flow rate of 10 ml/min. The results of the lactoferrin recovered by this method is shown in Table 4, which tabulates the quality of purified lactoferrin samples as determined by gel electrophoresis, spectroscopy, and chromatographic performance on Mono S™ resin.

TABLE 4

Evaluation of purified LF preparations

| Sample (Run #) | Recovery (%) | SDS-PAGE(1) Purity/ Saturation/ Cleavage (%) | Spectroscopy(2) Purity/ Saturation (%) | Mono S(3) Peak III (%) |
|---|---|---|---|---|
| hLF(11) | 89 | >99/<5/<1 | >99/3.1 | >99.99/>99 |
| bLF(354) | 90 | >99/<5/<1 | >99/8.4 |  |
| rHLF$^b$(24) | 80 | >99/>90/<1 | >99/100 | >99.9/>99 |

1. Purity was determined by applying samples of at least 10 μg of protein to SDS-polyacrylamide (7% w/v) slab gel electrophoresis (SDS-PAGE). Protein bands were visualized by staining with Coomassie Brilliant Blue. Percentage of iron saturation of lactoferrin was determined by non-reduced, non-boiled SDS-PAGE. Cleavage of lactoferrin was determined by reduced SDS-PAGE.
2. Purity was determined by absorbance spectrum analysis; for calculations, we used an A 0.1%, 1 cm at 280 nm of 1.1 for unsaturated (apo) LF, an A 0.1%, 1 cm at 280 nm of 1.4 for saturated (Fe) LF, and an A 0.1%, 1 cm at 465 nm of 0.056 for Fe hLF. $b$rhLF represents transgenic recombinant hLF purified from the milk of transgenic mice.
3. Purity was determined by applying 1 mg of protein on a Mono S™ (1 ml) column with a full scale sensitivity of 0.01. Nativity (see below) of hLF was analyzed by applying 50 μg of protein on the column and expressed as the % of total hLF that eluted at the peak III position (0.7 NaCl). The elution program was a linear salt (0–1M NaCl) gradient in 30 ml of 20 mM sodium phosphate, pH 7.5.

bLF eluted as a single peak with a small shoulder at approximately 0.8M NaCl.

Experiments with purified hLF and bLF, and hLF-spiked bovine milk on Mono S™ indicated that separation of transgenically produced rhLF from bLF can be accomplished by the use of a salt gradient elution or stepwise elution with buffers of increasing ionic strength (salt concentration). Transgenic rhLF produced in the milk of transgenic mice eluted at the same ionic strength as hLF derived from human milk.

Evaluation of Purified hLF Preparations by Mono S™ Chromatography

During the course of purification studies with transgenic rhLF from mouse milk (linear gradient of 0–1M NaCl in 20 mM sodium phosphate, pH 7.5 on a Mono S™ column), we observed that at least approximately 95% of transgenic rhLF was eluted at 0.7M NaCl, whereas commercially available hLF preparations (Sigma and Calbiochem) purified from human milk eluted as three peaks at approximately 0.5, 0.6, and 0.7M NaCl (denoted hLF peaks I, II, and III). hLF that was purified from fresh human milk always eluted at approximately 0.7M NaCl. bLF elutes at approximately 0.8M NaCl. Table 5 shows the elution patterns of various lactoferrin and other preparations on a Mono S™ column.

TABLE 5

Elution pattern of LF and other preparations on a Mono S™ column

| Preparation (FPLC Run No.) | Concentrations of NaCl (M) at which a peak is eluted (percentage of bound protein eluting at this position) | | |
|---|---|---|---|
| hLF Sigma 1(352) | 0.54(18) | 0.63(38.7) | 0.72(43.6) |
| hLF Sigma 2(353) | 0.53(30.2) | 0.63(49) | 0.71(19.8) |
| hLF Sigma 3(1075) |  | 0.61(5.7) | 0.69(94.8) |
| Calciochem hLF(116) | 0.54(18) | 0.62(17.2) | 0.72(63.6) |
| hLF GPE 1(1067) 2 and 3 |  |  | 0.68(100 |
| hLF GPE 4 (1097) | 0.53(9.1) |  | 0.66(91.3) |
| Arg-mod. hLF GPE(30) | no binding |  |  |
| Arg-mod. bLF GPE | no binding |  |  |
| Fe hLF Sigma 1(396) | 0.52(2.6) | 0.61(18.8) | 0.70(78) |
| Fe hLF Sigma 2(62) |  | 0.60(4.6) | 0.68(95.1) |
| Fe hLF GPE(824) |  |  | 0.65(100) |
| Deglyc. hLF GPE |  |  | 0.7(>99) |
| Neura. hLF GPE(894) |  |  | 0.67(100) |
| Tryp. hLF GPE 1(149) |  | 0.50(19.3) | 0.57(80.3) | -(0) |
| Tryp. hLF GPE 2(152) | 0.39(2.3) | 0.48(49.3) | 0.58(46.5) | -(0) |
| Tryp. hLF GPE 3(165) | 0.38(7.2) | 0.47(81) | 0.58(7.3) | -(0) |
| Trans hLF GPE 1(1315) |  |  | 0.63(5.7) | 0.69(94) |
| Trans hLF GPE 2(248) |  |  |  | 0.66(>99) |
| 293 rhLF |  |  |  | 0.68 (>99) |
| 293 Unglyc. rhLF |  |  |  | 0.69 (>96) |
| bLF Sigma(351) |  |  |  | 0.77(100) |
| bLF GPE(421) |  |  |  | 0.76(100) |
| mLF GPE(1132) | 0.26(100) |  |  |
| mDF GPE(1136) | 0.22(100) |  |  |
| mTF Sigma(548) | no binding |  |  |
| hTF Sigma(57) | no binding |  |  |
| pLFGPE(577) | 0.52(100 |  |  |
| Sheep whey | <0.6 (100) |  |  |
| Goat whey | <0.6 (100) |  |  |

TABLE 5-continued

Elution pattern of LF and other preparations on a Mono S ™ column

| Preparation (FPLC Run No.) | Concentrations of NaCl (M) at which a peak is eluted (percentage of bound protein eluting at this position) |
|---|---|

50 μg of protein in 20 mM sodium phosphate, pH 7.5 (buffer A) was applied to a Mono S ™ olumn (Pharmacia HR5/5 containing 1 ml of resin) using the FPLC system (Pharmacia). After washing the column with 5 ml of buffer A, a linear salt gradient from 0–1.0 M NaCl in 30 ml of buffer A was applied at a flow rate of 1 ml/min. Peaks were monitored by absorption measurement at 280 nm with a full scale sensitivity of 0.01 using a flow cell of 0.2 cm. The following abbreviations are used: hLF Sigma 1, purified human milk-derived "native" hLF from Sigma; hLF Sigma 2, repeatedly frozen and thawed Sigma 1; HLF Sigma 3, a different lot of "native" hLF from Sigma; Calbiochem hLF, human milk-derived hLF from Calbiochem; hLF GPE 1, 2, and 3, hLF preparations with iron saturation levels of about 3% purified by strong cation exchange chromatography of fresh human milk samples of three donors with total iron saturation of 3%; hLF GPE 4, hLF purified from a human milk sample that had been stored for one week at 4° C.; FehLF Sigma 1 and 2, different lots of purified human milk-derived hLF that is fully saturated with iron by Sigma; Arg-mod. hLF GPR, purified human milk-derived hLF that has had Arg residues chemically modified; FehLF GPE, purified human milk-derived hLF saturated with Fe; Deglyc. hLF GPE, purified human milk-derived hLF that was completely deglycosylated with N-glycosidase; Neura. hLF GPE, purified human milk-derived hLF that has had sialic acid resdiues removed with neuraminidase; Tryp. hLF GPE 1, 2 , and 3, purified human milk-derived hLF that was incubated with trypsin (molar ratio hLF:trypsin was 7.5:1) for 1 minute, 3 hours and 24 hours, respectively followed by addition of soybean trypsin inhibitor; Trans. hLF GPE 1 and 2, hLF purified from the milk of mice harboring cDNA (codes for signal sequence of bovine aS1 casein fused to mature hLF) and genomic hLF transgene constructs expressing rHLF at 0.2 and 2.0 mg/ml, respectively; 293 rhLF, recombinant hLF expressed in tissue culture (293 cells); 293 Unglyc. rHLF, purified unglycosylated non-cleaved rHLF expressed by 293 cells in the presence of tunicamycin; bLF Sigma, purified bovine milk-derived bLF from Sigma; bLF GPE, bLF purified from fresh bovine milk by strong cation exchange chromatography; Arg-mod. bLF GPE, purified bLF that has had Arg residues chemically modified; mLF GPE, murine lactoferrin purified from fresh mouse milk by strong cation exchange chromatography on mouse milk (mDF is an 80 kD protein that belongs to the transferrin family); mTF Sigma; purified mouse (sero-) transferrin purchase from Sigma; hTF Sigma, purified human serotransferrin purchase from Sigma; pLFGPE, porcine lactoferrin purified from pig milk by strong cation exchange chromatography; Sheep whey and goat whey, whey fractions prepared from sheep and goat milk respectivley.

In the literature, Makino et al. (1992) *J. Chromato.* 579: 346 reports that three peaks of hLF that elute at 0.88, 0.97, and 1.05M NaCl represent diferric, monoferric, and apolactoferrin, respectively. However, our results of studies on saturation of hLF with iron indicate that two ferric atoms are coordinately incorporated in each hLF molecule, so that essentially all hLF from milk is either apolactoferrin or diferric. Native hLF (hLF purified from fresh human milk; only 3% iron saturated by absorbance measurement) and Fe-hLF (completely saturated with iron as determined by absorbance measurement and non-reduced, non-boiled SDS-PAGE) elute at exactly (within the limits of experimental resolution) the same position (approximately 0.7M NaCl) from a Mono S™ column at pH 7.5. Completely deglycosylated (with N-glycosidase), neuraminidase-treated, and native hLF elute at exactly (within the limits of experimental resolution) the same position (approximately 0.7M NaCl) from a Mono S™ column at pH 7.5.

The relative amount of hLF peaks I and II increased upon prolonged (4 days) dialysis of transgenic mouse whey. In addition, hLF peaks II and I appeared after limited tryptic proteolysis of native hLF (peak III) before degradation of hLF could be observed by non-reduced or reduced SDS-PAGE. Based on these observations, peaks II and I in hLF preparations may be generated by limited proteolysis of peak III (native hLF), such as with a serine protease cleaving at arginine. N-terminal proteolysis of hLF may be important as the biological activities of truncated hLF may be different than that of native hLF, such as binding of hLF to cellular receptors, in vivo clearance rate in the circulation, ability to inhibit endocytosis of chylomicron remnants, and/or antibacterial properties. In line with this idea were the results of the amino-terminal protein sequence analysis of hLF peaks I, II, and III present in commercially available purified hLF (see Table 6).

Table 6 (SEQ ID NOS:1–28) shows N-terminal sequence analysis of some of the proteins in Table 5.

TABLE 6

| | | | | |
|---|---|---|---|---|
| HLF GPE 1 | GRRRRSVQWXAVSQPEATKXFQWQR | | | |
| HLF cDNA of GPE | GRRRRSVQWCAVSQPEATKCFQWQRNMRKVRGPPVSCIKRDSPIQCIQAIAENR | | | |
| apoE c | | 133 LRVRLASHLRKLRKRLLR 150 | | |
| HLF M.B. a | identical | QWQSNVRRM | | |
| HLFcDNA Rado | GRRR-SVQWCAVSNPEAT | identical | VSCLKR identical | R |
| Lactoferricin H b | GRRRRSVQWCA*VSQPEATKCFQWQRNMKVRGPPVSCIKRDSPIQCI (5558 Da) | | | |
| Lactoferricin H b synthetic analog | | TKXFQWQRNMRKVRGPPVSXIKD | | |
| Lactoferricin B b | | FKCRRWQWRMKKLGAPSITCVRRAF | (3126 Da) | |
| Lactoferricin B b synthtic analog | | FKXRRWQWRMKKLGAPSITXVRRAF | | |
| Calbio.peak III | GRRRRSVQ | | | |
| Calbio.peak II | RRRSVQWXAVS | | | |
| Calbio.peak I | RRSVQWXAVSQ | | | |
| HLF GPE 2 peak III | GRRRRSVQW | | | |
| HLG GPE 2 peak II ? | | | | |
| Trans HLF GPE 1. | GRRRRSVQWXAVSQP | | | |
| Trans HLF GPE 2. | GRRRRSVQWXAVSQPEAKXFQ | | | |
| MLF GPE | KATTVRWXAVSNSEEEKXLRWQ | | | |
| MLF cDNA Teng | KATTVRWCAVSNSEEEKCLRWQNEMRKVGGPPLSCVKKSSTRQCIQAIVTNR | | | |
| MDF | KAVRVQWXAVSNEE | | | |
| MTF Sigma | VPDKTVKWXAVXEHXNIK | | | |
| HTF DNA? | VPDKTVRWCAVSEHEATKCQSFRDHMKSVIPSDGPSVACVKKASYLDCI | | | |
| HTF M.B. a | identical | MEATKCESFRD | | |
| BLF cDNA Pier ce | APRKNVRWCTISQPEWEKCRRWQWRMKKLGAPSITCVRRAFALECIRAIAEKK | | | |
| BLF Barnyard a | identical | IAQPE | | |
| BTF Barnyard a | DPERTVRWCTI | | | |
| OLF a | APRKNVRWCAISPPEGSRCYQWQKKMRRM | | | |

TABLE 6-continued

| | | |
|---|---|---|
| OTF | a | APPKSVRIWCTISSPEEKKCNNLRDLTQQE |
| PLF | ? | APKKGVRWCVISTAEYSKCRQWQSKIRR - - TNPIFCIRRASPTDCCIRAI |
| PTF | ? | AQKTVRWCTISNQEANK |

On the basis of the elution patterns of Table 5, the N-terminal protein sequence data of Table 6 as well as those of transferrins and lactoferrins published in the literature, we conclude that the amino-terminal sequences of transferrins/lactoferrins determine the binding characteristics of these molecules to strong cation exchange resins and that native (peak III) hLF can be purified from degradation products (peaks I and II) by strong cation exchange chromatography. Thus, strong cation exchange chromatography can be used for quality control assessment of hLF by separating and quantitatively detecting the amounts of native hLF and degradation products (peaks I and II material), and for preparative purification of native hLF from such degradation products, such as for pharmaceutical formulation of homogeneous native hLF or purified peak I or peak II material, if desired. On the basis of the differential elution patterns of nonhuman and human lactoferrin species as presented in Table 5 as well as from experiments with mixtures of purified hLF and bLF, and hLF-spiked bovine milk on Mono S™ (see below), we also conclude that separation of transgenically produced rhLF from nonhuman lactoferrin (e.g., bLF) can be accomplished with strong cation-exchange chromatography by the use of a salt gradient or stepwise elution with buffers of increasing ionic strength (salt concentration). It is to be noted that transgenic rhLF produced in the milk of transgenic mice eluted at the same ionic strength as hLF derived from human milk. Furthermore, all proteins from sheep and goat whey fractions that had bound to Mono S™ were eluted an NaCl concentrations lower than 0.6M NaCl (Table 5). This indicates that transgenic rhLF can be resolved from sheep and goat lactoferrin species by strong cation-exchange chromatography.

Chromatographic Separation of hLF and bLF

Table 7 shows the elution patterns of hLF and bLF on Mono S™ with linear salt gradients demonstrating the different salt strengths at which hLF and bLF elute.

TABLE 7

Elution pattern of HLF and BLF on Mono S ™

| FPLC run no. | Buffer | hLF (M NaCl) | bLF (M NaCl) | Difference bLF - hLF (M NaCl) |
|---|---|---|---|---|
| 943 | 20 mM Na acet pH 5.0 | 0.72 | | |
| 944 | " | | 0.78 | |
| 945 | " | 0.72 | 0.78 | 0.06 |
| 955 | 20 mM Na phos pH 6.0 | 0.69 | | |
| 956 | " | | 0.76 | |
| 957 | " | 0.69 | 0.76 | 0.07 |
| 934 | 20 mM Na phos pH 7.5 | 0.66 | | |
| 938 | " | | 0.73 | |
| 940 | " | 0.66 | 0.73 | 0.07 |
| 948 | 20 mM eth am pH 9.5 | 0.57 | | |
| 949 | " | | 0.63 | |
| 950 | " | 0.57 | 0.63 | 0.06 |

Fifty μg of protein (HLF Sigma 3 and/or BLF Sigma) in buffers of different pH (buffer A) was applied to the column (Pharmacia HR5/5 containing 1 ml of equilibrated resin beads) using the FPLC system of Pharmaica. After washing the column wth 5 ml of buffer A, a linear salt gradient from 0–1.0 M NaCl in 30 ml of buffer A was applied at a flow rate of 1 ml/minute. Peaks were monitored by absorption measurement at 280 nm.

Figure 1B:
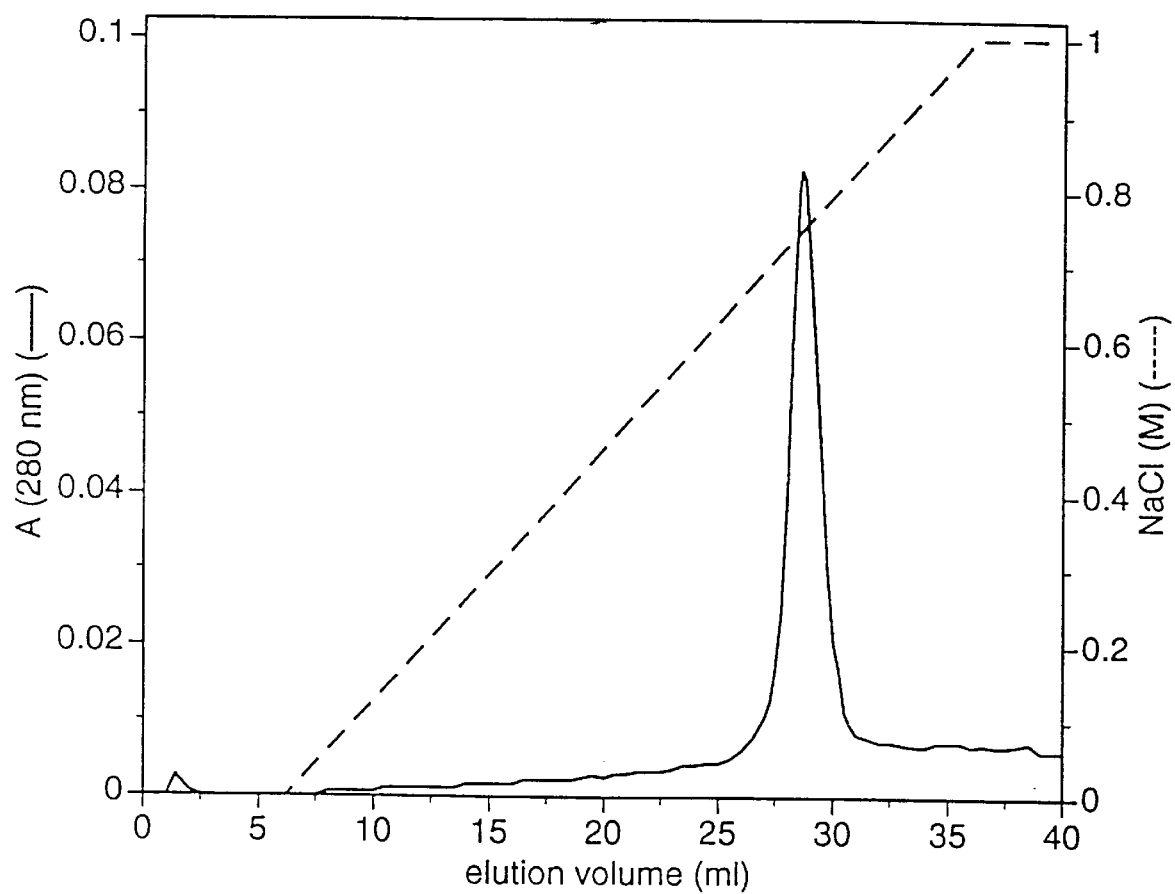

Since the difference in elution patterns was relatively pH insensitive at the pH values tested, the elution pattern of hLF and bLF at near physiological pH (pH 7.5) was determined and is shown in FIG. 1. 100 μg of HLF Sigma 3 (panel A) or BLF Sigma (panel B) in buffer A (20 mM sodium phosphate, pH 7.5)was applied to the Mono S™ column (Pharmacia HR5/5 containing 1 ml of equilibrated resin beads) using the FPLC system of Pharmacia. After washing the column with 5 ml of buffer A, a linear salt gradient from 0–1.0M NaCl in 30 ml of buffer A was applied at a flow rate of 1 ml/minute. Peaks were monitored by absorption measurement at 280 nm (full scale 0.02).

Figure 2A:
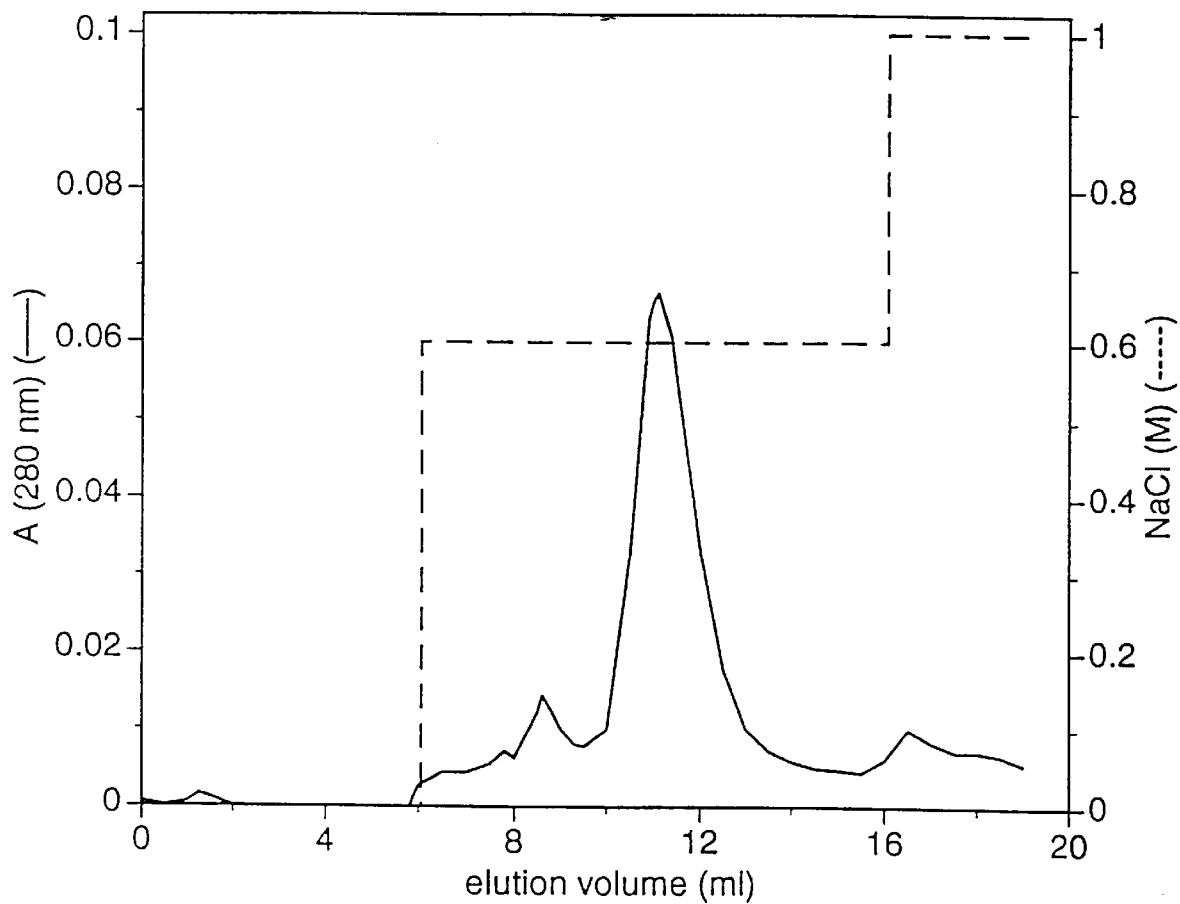
FIG. 2 shows the elution profiles of lactoferrin from a strong cation exchange resin, Mono S™, by stepwise elution. Panel A show the stepwise elution profile of hLF. Panel B shows the stepwise elution of bLF.
Figure 2B:
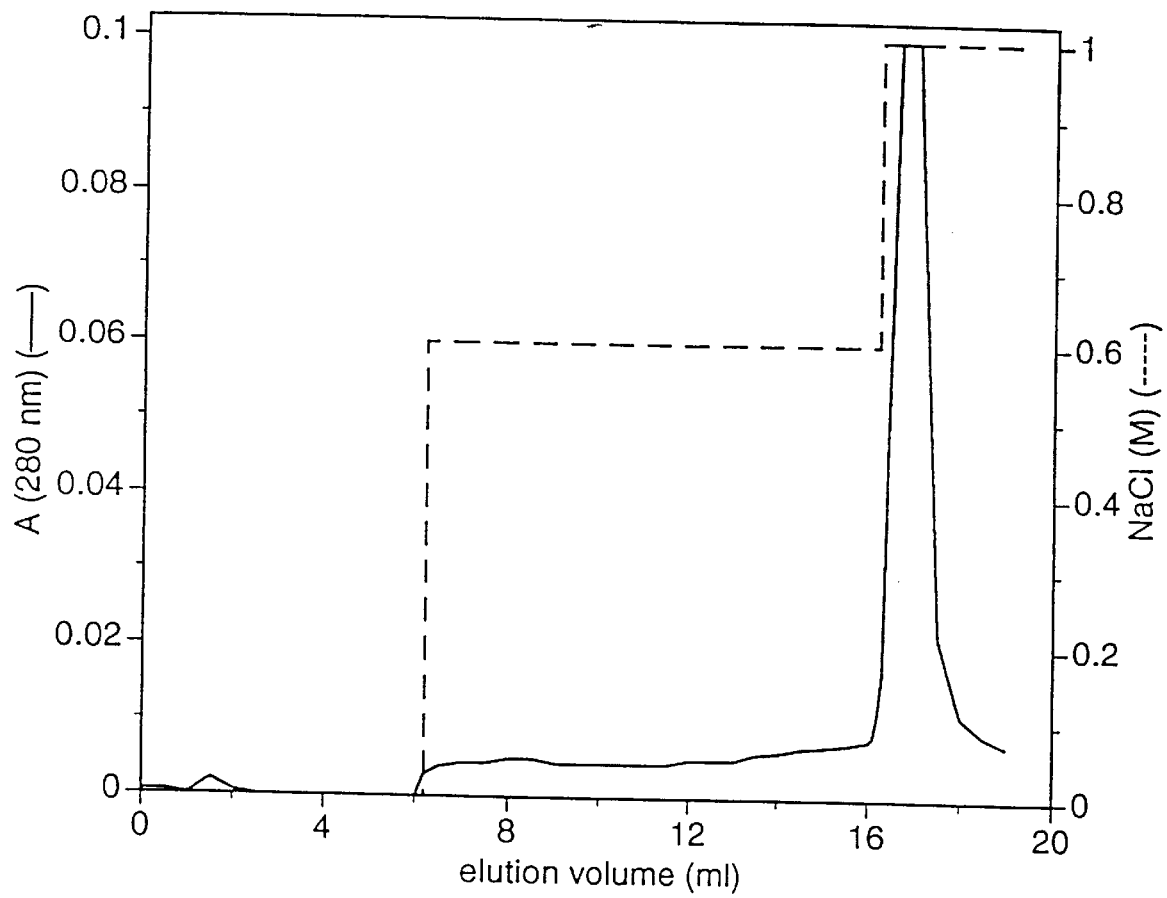

FIG. 2 shows the differential elution pattern of hLF and bLF on Mono S™ with a stepwise elution program (sequential increases of salt concentration to 0.6 and 1.0 M NaCl). 100 μg of hLF Sigma 3 (panel A) or bLF Sigma (panel B) in buffer A was applied to the Mono S™ column (Pharmacia HR5/5 containing 1 ml of equilibrated resin beads) using the FPLC system of Pharmacia. After washing the column with 5 ml of buffer A, the salt concentration was stepwise increased from 0M to 0.6M NaCl in buffer A, pH 7.5 at a flow rate of 1 ml/minute. After 10 minutes, another stepwise increase from 0.6M to 1.0M NaCl in buffer A was applied at 1 ml/minute. Peaks were monitored by absorption at 280 nm.

Figure 3A:
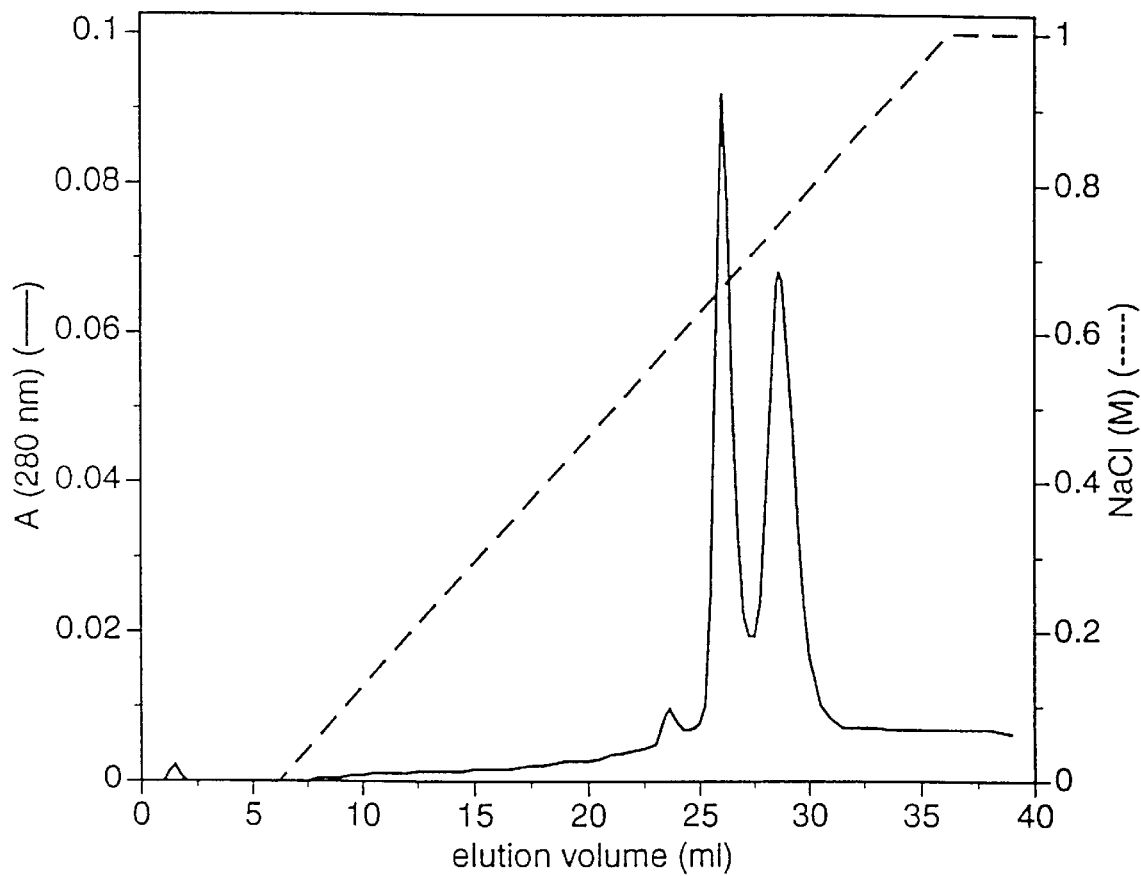
FIG. 3 shows chromatographic resolution of hLF from bLF on a strong cation exchange resin. Panel A shows elution by linear salt gradient elution. Panel B shows elution by a stepwise elution mode.
Figure 3B:
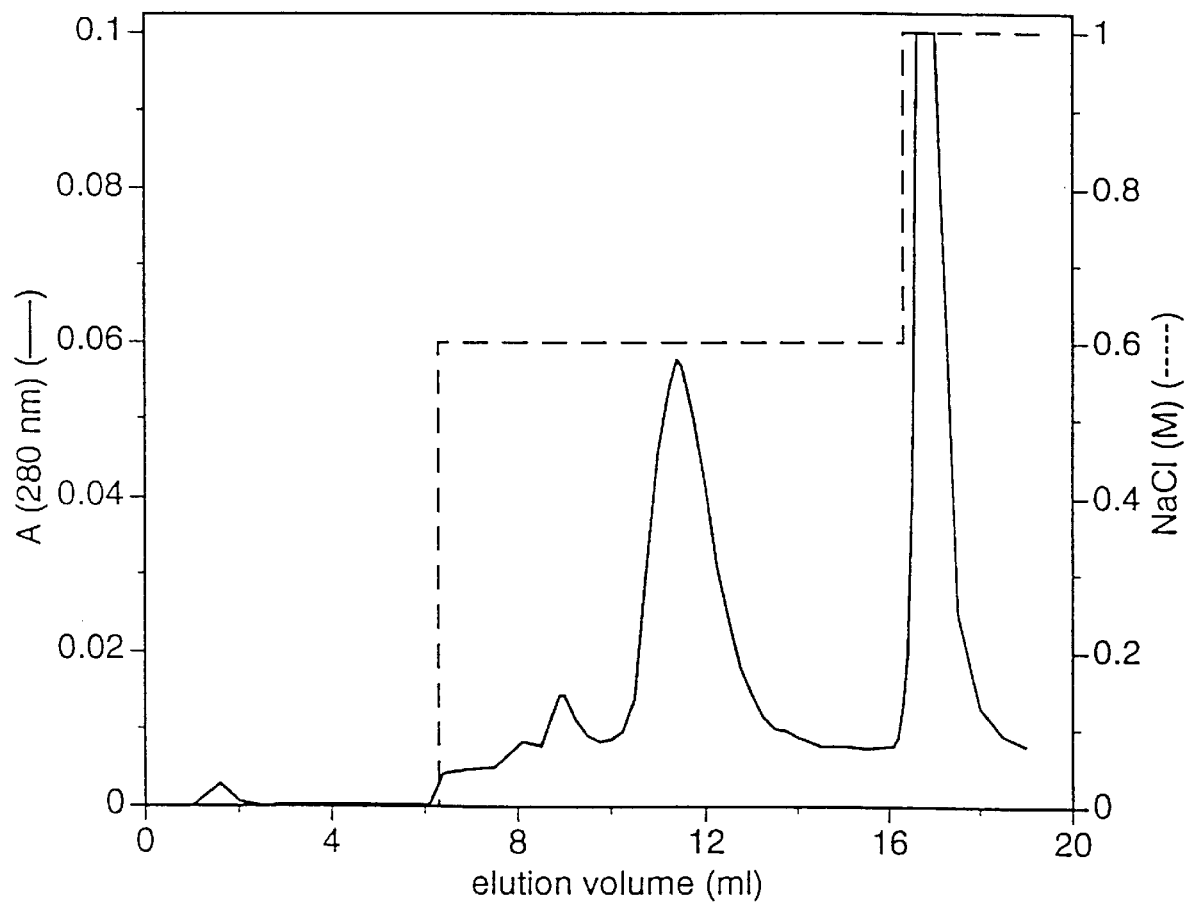

FIG. 3 shows the substantial purification of hLF and bLF by resolution of a mixture of purified proteins on a Mono S™ column either with a linear salt gradient or stepwise elution. 100 μg of hLF and 100 μg of bLF were each applied to the column in buffer A and eluted by linear NaCl gradient (panel A) or stepwise elution (panel B) as described above. The major hLF peak elutes at 0.67M NaCl and the major bLF peak elutes at 0.75M NaCl under the conditions used for linear gradient elution (FIG. 3, panel A) With the stepwise elution program, the major hLF peak elutes in 0.6M NaCl step buffer and the major bLF peak elutes in the 1.0M NaCl step buffer (FIG. 3, panel B).

Figure 4A:
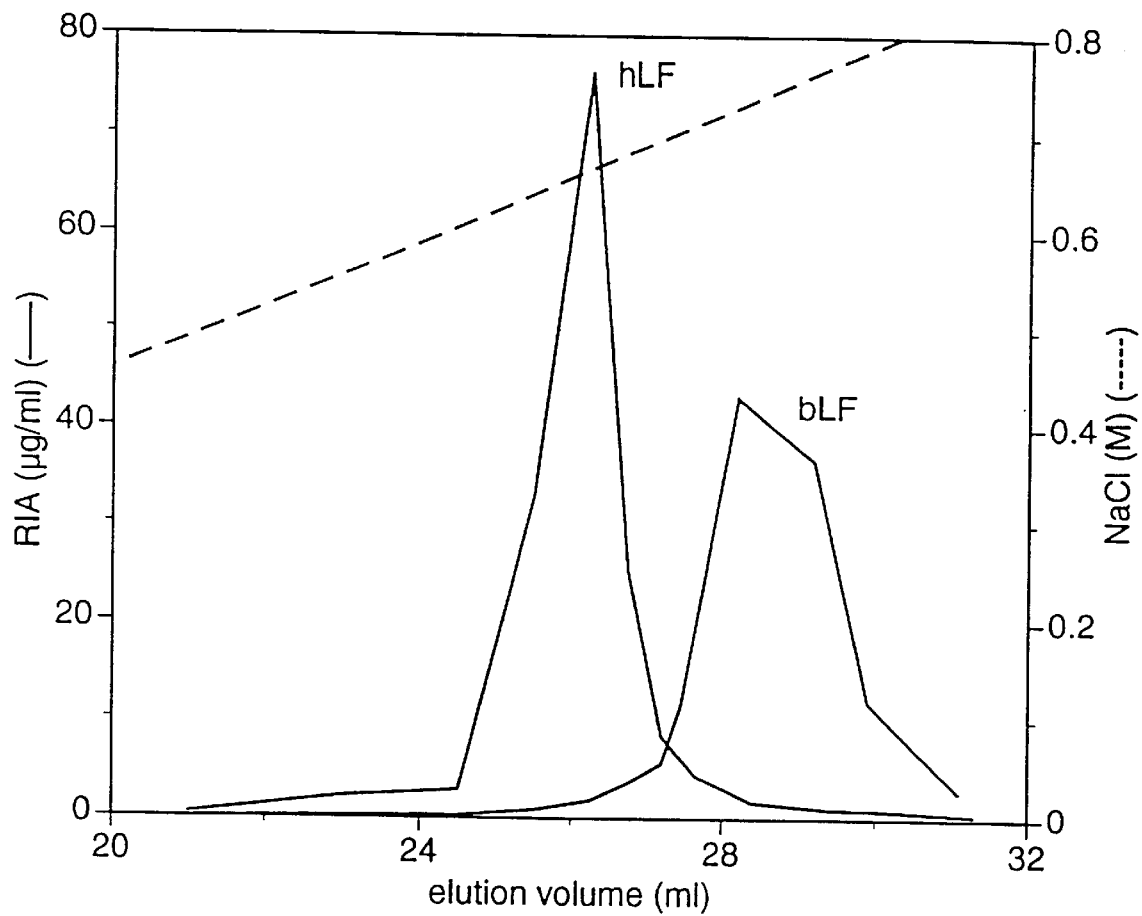
FIG. 4 shows specific radioimmunoassays for hLF and bLF in eluted fractions. Panel A shows results for linear salt gradient elution. Panel B shows results for stepwise elution.
Figure 4B:
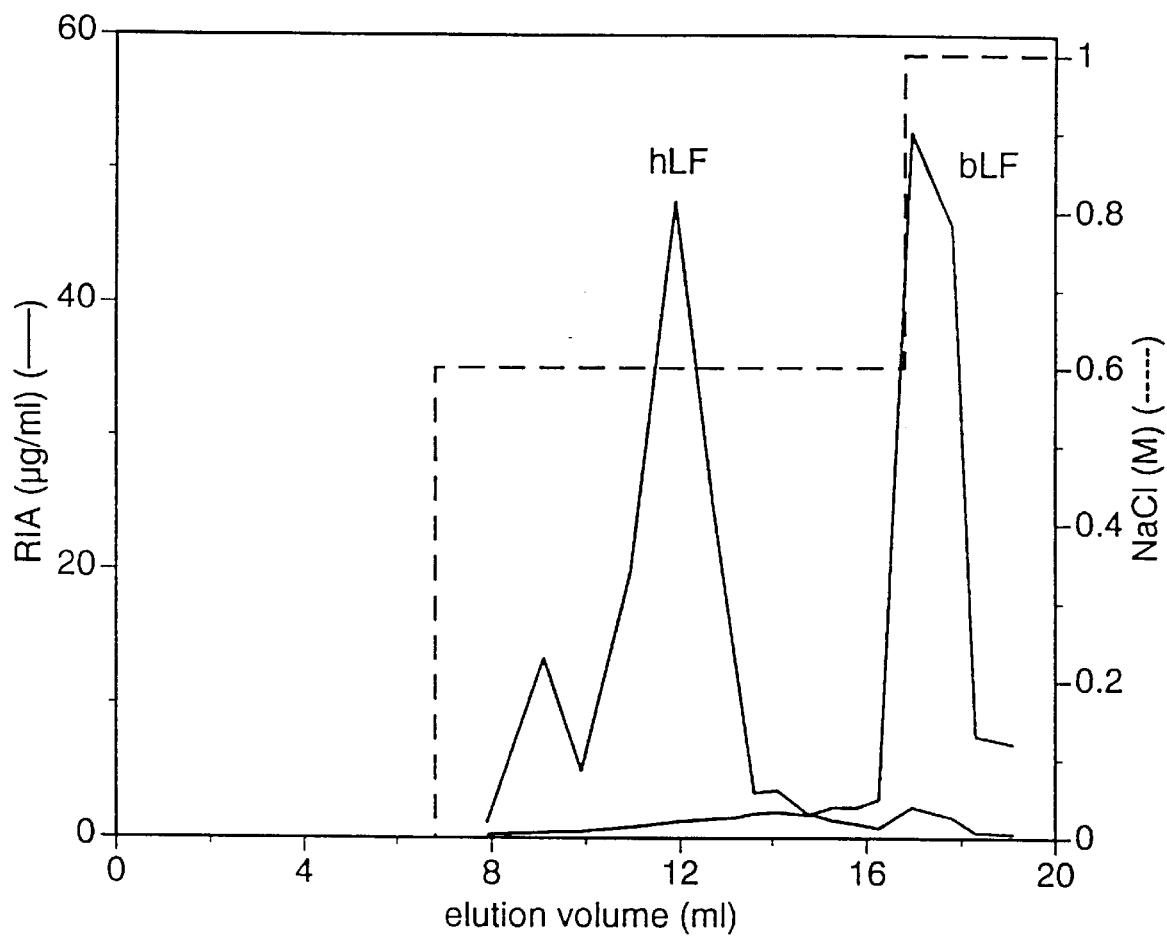

FIG. 4 shows specific radioimmunoassays for hLF and bLF in elution fractions of the gradient-wise (panel A) and stepwise (panel B) elutions under FIG. 3. The purity of top fractions of hLF and bLF exceeds approximately 95% as determined by RIA (i.e., less than about 5% cross contamination). Resolution of hLF from bLF was somewhat better with stepwise elution than linear gradient elution.

Figure 5A:
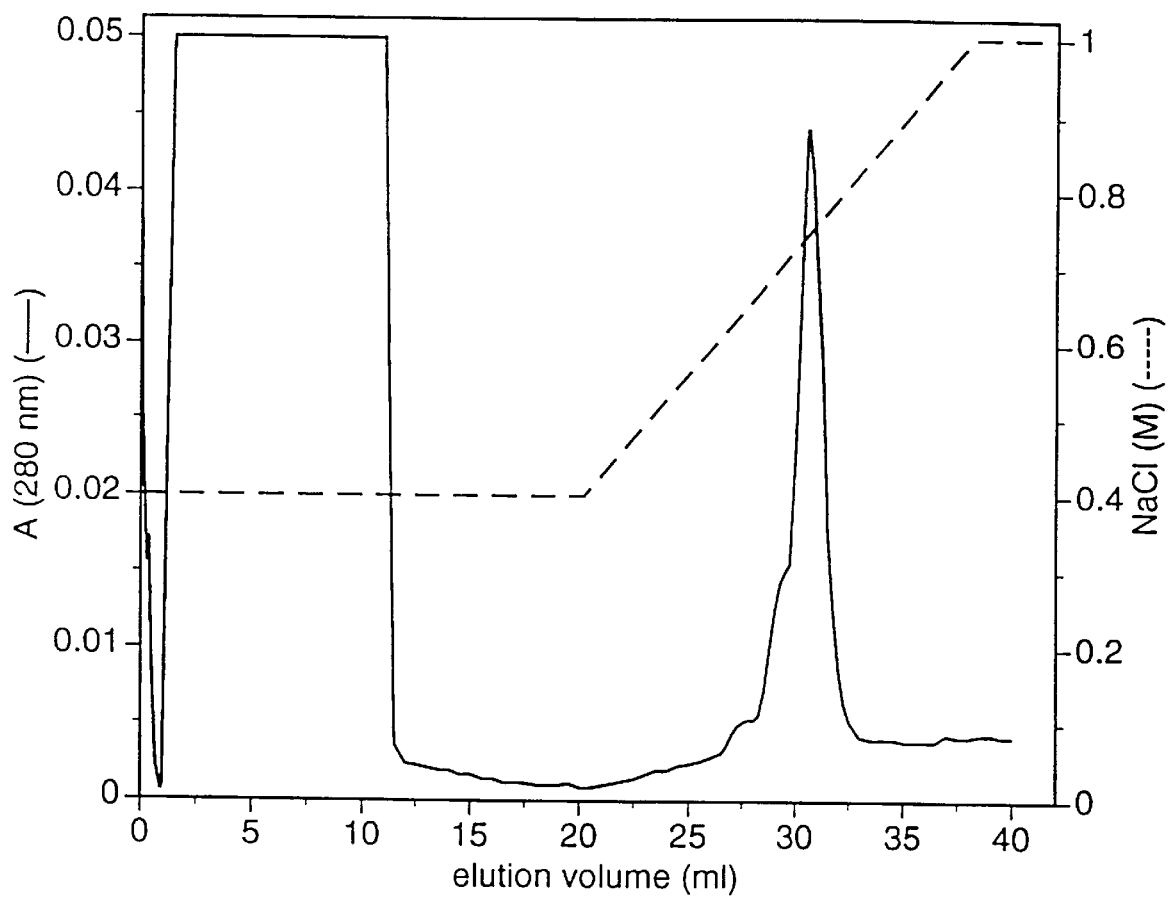
FIG. 5 shows chromatographic resolution of hLF from bLF in hLF-spiked bovine milk chromatographed on a Mono S™ column. Panel A shows results for control (unspiked) bovine milk. panel B shows results for hLF-spiked bovine milk.
Figure 5B:
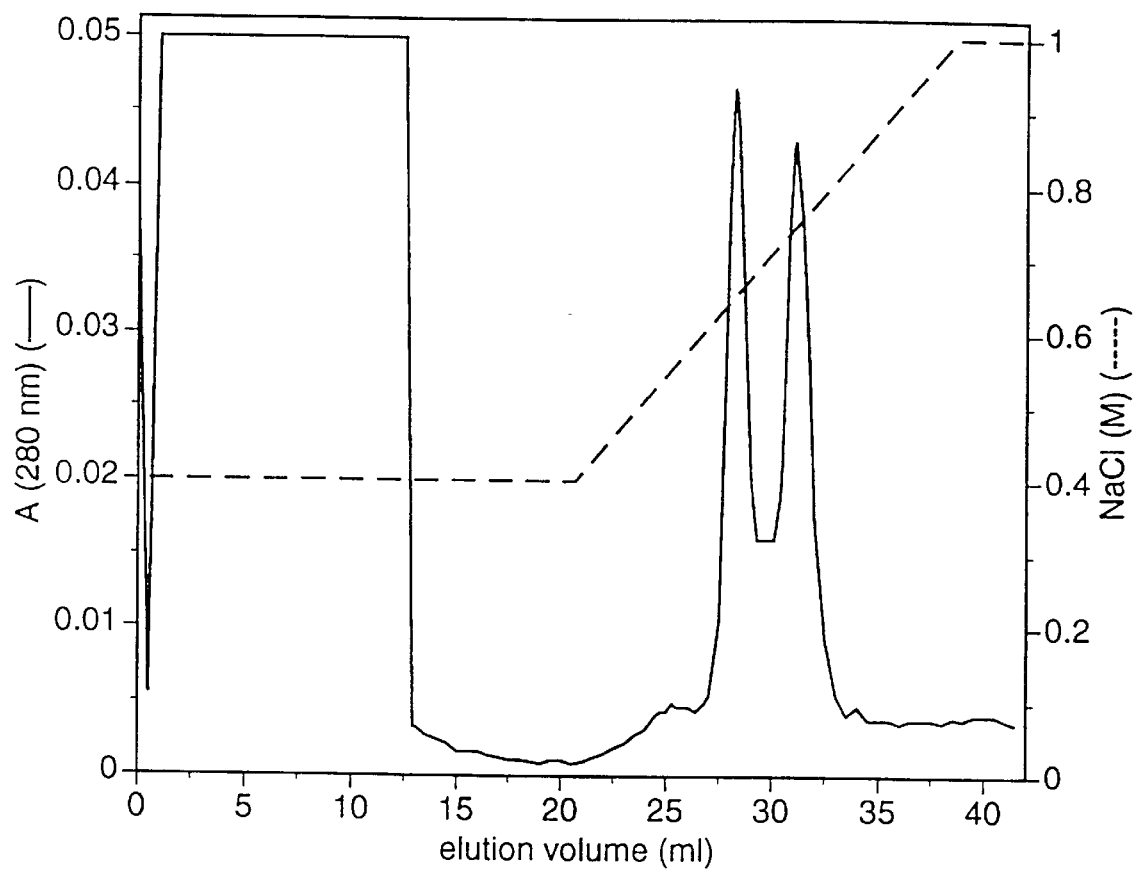
Figure 6A:
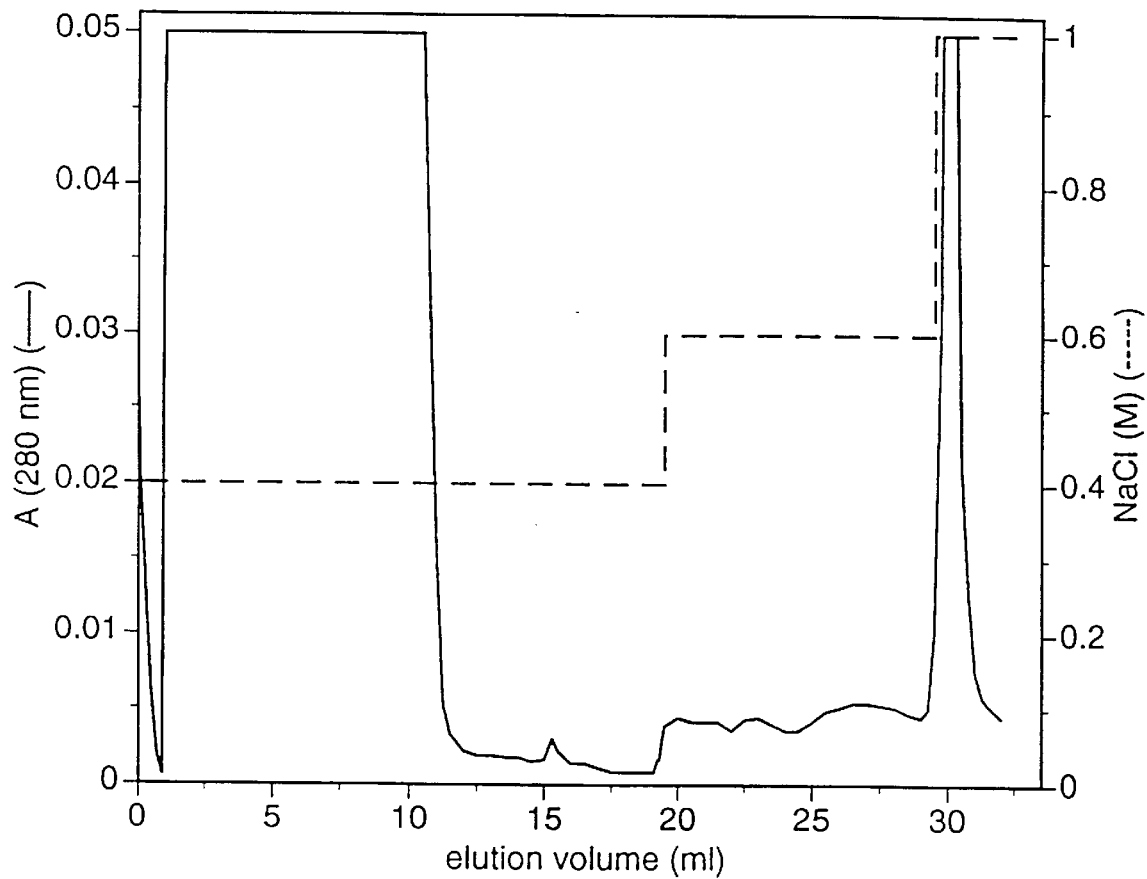
FIG. 6 shows the chromatographic resolution of hLF from bLF in hLF-spiked bovine milk chromatographed on a Mono S™ column with stepwise salt elution. Panel A shows (unspiked) control bovine milk. Panel B shows hLF-spiked bovine milk.
Figure 6B:
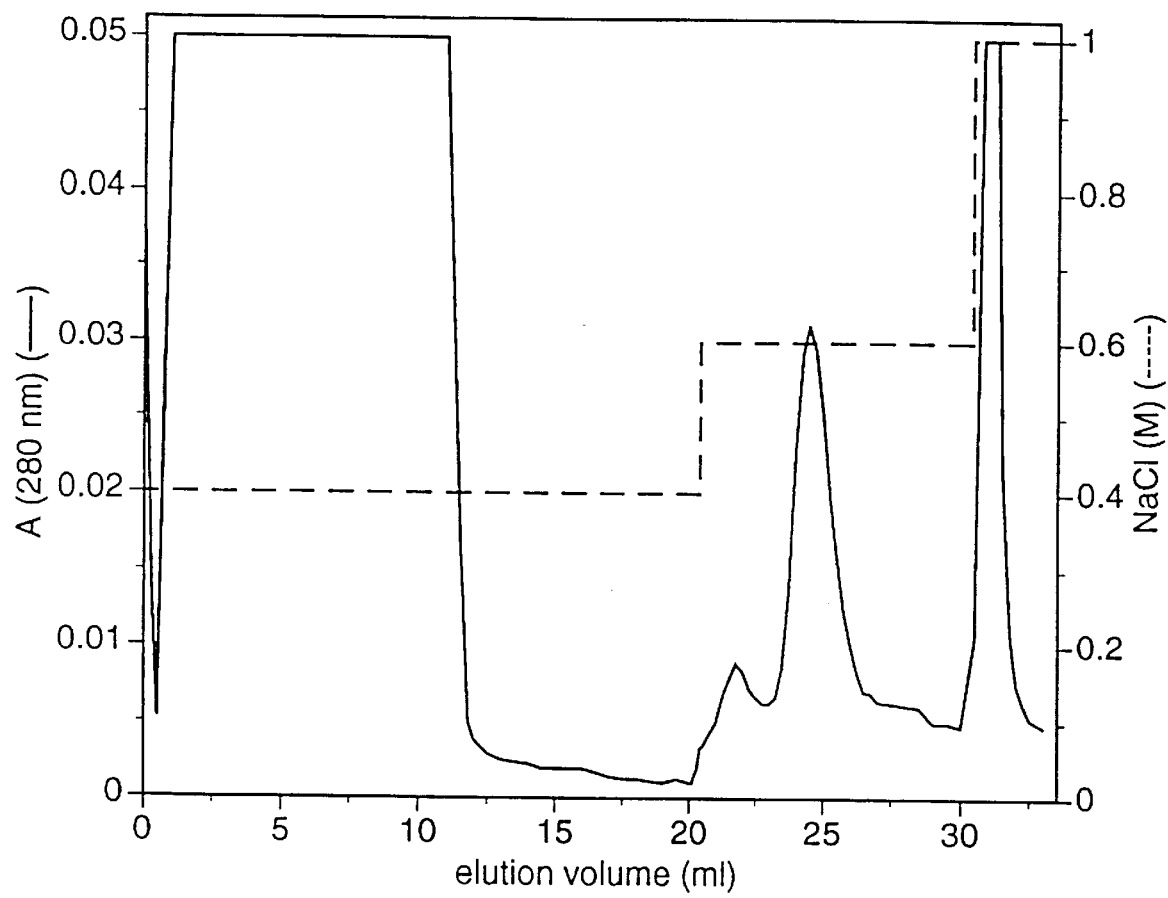

Purified hLF was added to raw bovine milk and used to determine the chromatographic purification of hLF from bLF in bovine milk by using a strong cation exchange resin. Bovine milk to which sodium phosphate, pH 7.5 (20 mM), NaCl (0.4M), Tween-20 (0.02%) and either hLF (100 μg/ml) or buffer alone had been added was stirred for 20 minutes at room temperature (final pH was 6.6). Skimmed milk (obtained by centrifugation at 15,000×g for 30 minutes at 4° C.) was adjusted to pH 4.7 with 1N HCl and incubated at 40° C. for 30 minutes. Whey fraction (obtained by centrifugation at 15,000×g for 30 minutes at 4° C.) was adjusted to pH 7.5 with 1N NaOH, and further clarified by centrifugation at 15,000×g for 5 minutes at 20° C. followed by filtration through a 0.22 μm filter. One ml samples of whey were applied to the Mono S™ column equilibrated with 0.4M NaCl, 20 mM sodium phosphate, pH 7.5. The column was then washed with 18 ml of 0.4M NaCl, 20 mM sodium phosphate, pH 7.5 at 1 ml/min. Peaks were monitored by absorption measurement at 280 nm (full scale 0.01). FIG. 5 shows the chromatograms when a linear salt gradient from 0.4–1.0M NaCl in 18 ml of 20 mM sodium phosphate, pH 7.5 was subsequently applied; panel A shows bovine whey with bLF only (unspiked) and panel B shows bovine whey containing bLF and hLF (spiked). FIG. 6 shows the chromatograms when the salt concentration was stepwise increased from 0.4M to 0.6M NaCl in 20 mM sodium phosphate, pH 7.5; after 10 minutes, another stepwise increase from 0.6M to 1.0M NaCl in 20 mM sodium phosphate, pH 7.5 was applied; panel A shows bovine whey with bLF only (unspiked) and panel B shows bovine whey containing bLF and hLF (spiked). The resolution of hLF from bLF with stepwise elution was better than that seen with a linear salt gradient under the conditions tested.

The volume as well as salt strength of an elution buffer required to start and establish complete elution of hLF relate to the amount of hLF bound to the column. A small increase (e.g., stepwise from 0.4M to 0.5M NaCl) in salt concentration will readily and preferentially start elution of hLF when the column is loaded with increasing amounts of hLF. It was observed that the more hLF bound to the resin, the lower the salt concentration required to start elution of hLF and the greater the tailing of the hLF peak that occurred.

Effects of Salt Concentration on Elution Volume

100 μg of hLF were loaded on a Mono S™ column and elution buffers of varying NaCl concentration in 20 mM sodium phosphate, pH 7.5 were applied to completely elute the bound hLF. Table 8 shows the volumes (in ml) of each of the salt concentrations required for complete elution of the hLF.

TABLE 8

Elution Volume Dependence on Salt Concentration

| NaCl (M) | Volume (ml) required for complete elution |
|---|---|
| 0.4 | 165 |
| 0.5 | 17 |
| 0.6 | 4.9 |
| 0.7 | 2.5 |
| 0.8 | 1.7 |
| 0.9 | 1.5 |

With lower salt concentrations, the sharpness of the peaks eluted was noted to decrease. These results indicate that the volume of washing buffer (e.g., 0.4M NaCl) during large scale purification should be limited, since washing the resin with large volumes relative to the volume of the packed resin under the tested conditions would completely elute the bound hLF.

Scale-up Purification of hLF

Varying amounts of hLF were loaded onto a 1 ml Mono S™ column and a linear salt gradient (0–1.0M NaCl in 30 ml of 20 mM odium phosphate, pH 7.5) was applied at 1 ml/min. The NaCl concentration at which elution of hLF was observed to begin as well as that at which hLF elution was complete was recorded. Table 9 shows the results.

TABLE 9

Elution patterns of varying amounts of HLF bound to a Mono S ™ column

| Amount of hLF bound to Mono S ™ | NaCl concentration (M) at which elution starts/ appears complete | Peak shape |
|---|---|---|
| 50 μg (run 1144) | 0.69 | very sharp (A = 0.01) 95% protein in 1.5 ml |
| 8,500 μg (run 1145) | 0.54/0.73 | broad (A = 0.5) 95% protein in 4.5 ml |
| 20,000 μg (run 1152) | 0.44/0.7 | broader (A = 1.0) 95% protein in 7.2 ml) |
| 36,500 μg (run 1146) | 0.29/0.73 | very broad (A = 2.0) 95% protein in 11.0 ml |

Figure 7:
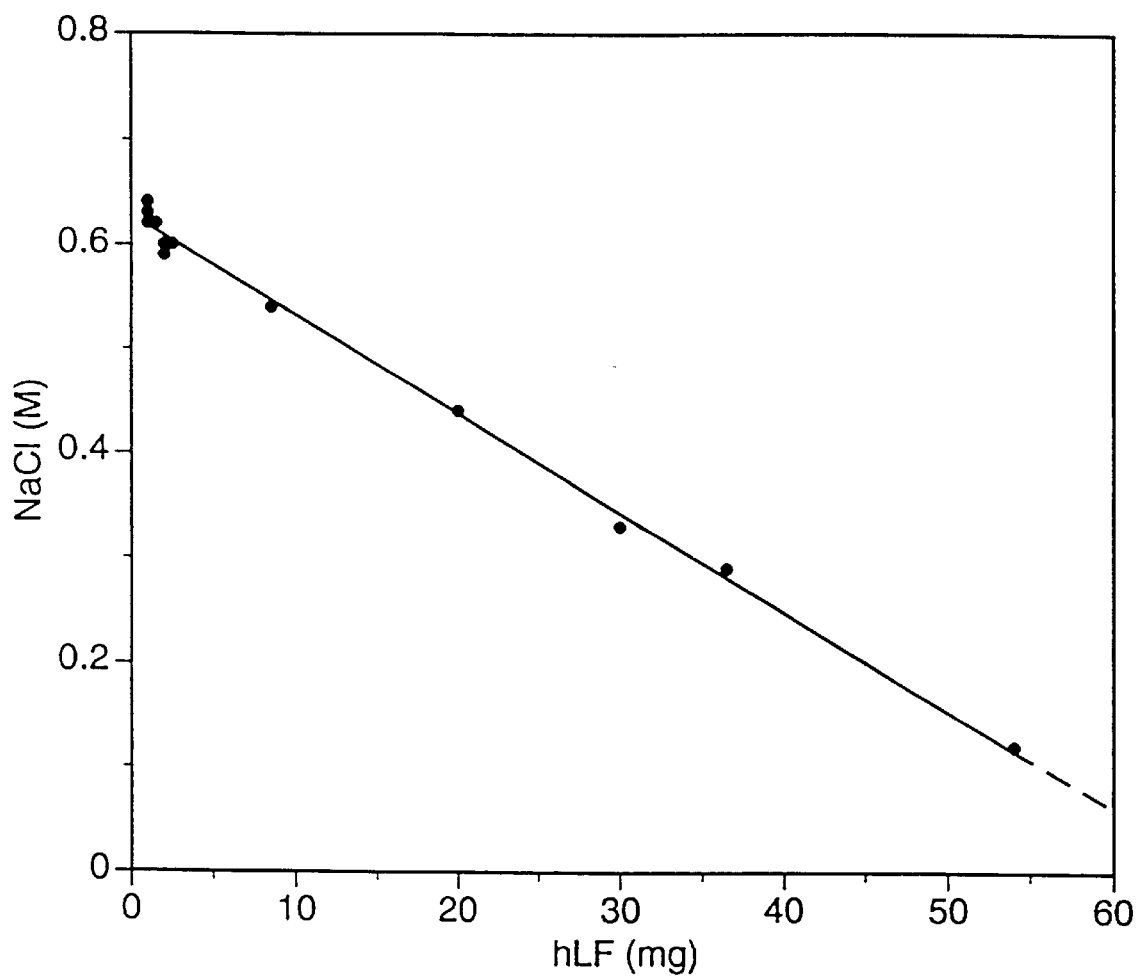
FIG. 7 shows the relationship between the amount of hLF bound to a Mono S™ column and the NaCl concentration at which elution of hLF was observed to begin when a linear salt gradient was applied.

FIG. 7 depicts the relationship between the amount of hLF bound to a 1 ml Mono S™ column and the NaCl concentration at which elution of hLF was observed to begin when a linear salt gradient (0–1.0M NaCl in 30 ml of 20 mM sodium phosphate, pH 7.5) was applied at 1 ml/min. The data of FIG. 7 give an indication of the maximum binding capacity (mg hLF bound per ml of resin) of Mono S™. Experiments with S Sepharose™ Fast Flow produced similar results.

Affinity Chromatography on Concanavalin A

Glycosylation differences which exist between hLF and bLF can be used to separate hLF to bLF by lectin chromatography. hLF bound to Con A could be completely eluted with 50 mM α-methyl-D mannopyranozide in 50 mM Tris Cl, pH 8.0, 0.14 M NaCl, whereas bLF was not significantly eluted, even when 200 mM α-methyl-D mannopyranozide was used. Con A chromatography can thus be used to separate hLF from bLF, such as removing traces of bLF in hLF preparations made by strong cation exchange chromatography i.e., an alternative to rechromatography on a strong cation exchange resin. Examples of strong cation excange resins include, but are not limited to:

| RESIN | SUPPLIER |
|---|---|
| S Sepharose Fast Flow | Pharmacia |
| SP Sephadex C-50 | Pharmacia |
| SP Sephadex C-25 | Pharmacia |
| Mono S ™ | Pharmacia |
| SP Sepharose Fast Flow | Pharmacia |
| SP Sepharose Big Beads | Pharmacia |
| A9 50 W X2 | BioRad |
| A9 50 W X4 | BioRad |
| A9 50 E X8 | BioRad |
| A9 50 W X12 | BioRad |
| A9 50 W X16 | BioRad |
| Protein Pak SP 15 HR | Millipore/Waters |
| Protein Pak SP 40 HR | Millipore/Waters |
| Parcosil PepKat | Serva |
| Parcomer PekKat | Serva |
| Fractogel EMD SO$_3$ 650 (M) | Merck |

Although the present invention has been described in some detail by way of illustration for purposes of clarity of understanding, it will be apparent that certain changes and modifications may be practiced within the scope of the claims.

We claim:

1. A method for substantially purifying human lactoferrin from milk, comprising the steps of:
   contacting milk or a milk fraction containing human lactoferrin with a strong cation exchange resin under elevated ionic strength conditions which are at least 10 mM higher in monovalent cation concentration than milk for a binding period forming human lactoferrin-resin complexes;
   removing the milk or milk fraction which remains unbound and recovering the human lactoferrin-resin complexes; and
   eluting the human lactoferrin from the recovered human lactoferrin-resin complexes with a salt solution having an ionic strength sufficient to elute the human lactoferrin from the human lactoferrin-resin complexes.

2. A method according to claim 1, wherein said step of contacting said milk or milk fraction with said strong cation exchange resin is conducted with a limiting amount of said strong cation exchange resin which has a binding capacity approximately equal to or less than the expected amount of human lactoferrin in the milk or milk fraction.

3. A method according to claim 1, wherein the milk or milk fraction is adjusted to approximately 0.35–0.4M salt by the addition of NaCl or KCl prior to contacting the milk or milk fraction with said strong cation exchange resin.

4. A method according to claim 1, wherein transgenic bovine milk whey is the milk fraction used for contacting with said strong cation exchange resin.

5. A method according to claim 1, comprising the further intermediate step of washing the recovered human lactoferrin-resin complexes with a wash buffer prior to eluting he human lactoferrin.

6. A method of claim 5, wherein the recovered human lactoferrin-resin complexes are poured into a column.

7. A method according to claim 1, wherein the strong cation exchange resin is selected from the group consisting of Mono S™ and S Sepharose™.

8. A method according to claim 7, wherein human lactoferrin is eluted and separated from bovine lactoferrin by a salt gradient.

9. A method according to claim 1, wherein the salt solution for eluting the human lactoferrin is at least 0.4M NaCl or at least 0.4M KCl.

10. A method according to claim 1, wherein the human lactoferrin is eluted in a stepwise mode comprising an elution step having a salt solution which substantially elutes human lactoferrin without substantially eluting bovine lactoferrin.

11. A method according to claim 1, comprising the further step of recovering the eluted human lactoferrin, loading the recovered human lactoferrin on a strong cation exchange resin or concanavalin A resin, and eluting the human lactoferrin from the resin in substantially purified form.

12. A method according to claim 1, wherein the step of contacting the milk or milk fraction with the strong cation exchange resin is performed across a dialysis membrane which is substantially permeable to human lactoferrin.

13. A method according to claim 1, wherein the elevated ionic strength conditions which are at least 10 mM higher in monovalent cation concentration than milk are produced by the addition of exogenous NaCl or KCl and/or buffer to milk or a milk fraction to which a detergent has or has not been added.

14. A method according to claim 1, wherein human lactoferrin is purified from milk or a milk fraction containing bovine lactoferrin, whereby the human lactoferrin is isolated from bovine lactoferrin by differential elution with a salt solution.

15. The method of claim 1 further comprising the step of mixing the human lactoferrin with a carrier to form a pharmaceutical composition.

16. A method for purifying native human lactoferrin from hLF degradation products in a sample, comprising the step of contacting the sample with a strong cation exchange resin under binding conditions and eluting the native human lactoferrin as a resolvable peak by applying a salt gradient or in a stepwise mode and recovering the peak consisting essentially of native human lactoferrin having an intact amino terminal sequence.

17. A method according to claim 16, wherein the degradation products comprise human lactoferrin species which lack amino-terminal amino acids compared to a full-length human lactoferrin protein.

18. A method according to claim 16, wherein the degradation products elute at a lower salt concentration than that at which native human lactoferrin elutes.

19. A method for separating human lactoferrin from bovine lactoferrin in a sample, comprising contacting the sample with a strong cation exchange resin and eluting the human lactoferrin from the resin with a salt solution which preferentially elutes human lactoferrin but does not substantially elute bovine lactoferrin concomitantly with the human lactoferrin.

20. A method according to claim 19, wherein hLF and bLF are separated by stepwise increases of salt concentration.

21. A method according to claim 19, wherein hLF and bLF are separated by elution with a salt gradient.

22. A method according to claim 19, wherein the strong cation exchange resin is Mono S™ or Fast Sepharose S™, the binding conditions comprise elevated ionic strength which is at least 10 mM higher in monovalent cation concentration than milk, and elution of human lactoferrin is accomplished with a salt solution which preferentially elutes human lactoferrin but does not substantially elute nonhuman lactoferrin concomitantly with the human lactoferrin.

23. A method for isolating substantially pure recombinant human lactoferrin from the milk of a transgenic animal harboring a transgene which encodes the expression and secretion of recombinant human lactoferrin in its milk, comprising the steps of:

obtaining milk or a milk fraction of said transgenic animal containing recombinant human lactoferrin;

contacting said milk or milk fraction with a strong cation exchange resin under conditions for binding of the human lactoferrin to the resin;

eluting the recombinant human lactoferrin from the strong cation exchange resin with a stepwise salt gradient or linear salt gradient.

24. A method according to claim 23, wherein the strong cation exchange resin is Mono S™ or Fast Sepharose S™, the binding conditions comprise elevated ionic strength which is at least 10 mM higher in monovalent cation concentration than milk, and elution of human lactoferrin is accomplished by eluting with a salt solution of at least 0.5M NaCl.

25. A method according to claim 23, wherein the binding conditions are the milk or milk fraction adjusted to approximately 0.35–0.4M NaCl and elution is accomplished with a salt solution consisting essentially of at least 0.4M NaCl or KCl.

26. A method for removing LPS from a solution, comprising the step of contacting a solution containing LPS with a resin comprising immobilized hLF and recovering the portion of the solution that is bound to the resin comprising immobilized hLF.

27. A method of claim 26, wherein the resin comprising immobilized hLF is hLF covalently linked to Sepharose.

* * * * *

UNITED STATES PATENT AND TRADEMARK OFFICE
CERTIFICATE OF CORRECTION

PATENT NO. : 5,919,913
DATED : July 6, 1999
INVENTOR(S) : Jan H. Nuijens and Harry van Veen It is certified that error appears in the above-identified patent and that said Letters Patent is hereby corrected as shown below:

On the title page:

[75] Inventors: Jan H. Nuijens, MV Heiloo; Harry Van Veen, NB Boskoop, both of Netherlands In the Claims:

In Claim 5, line 4, please replace the word "he" with --the--.

Signed and Sealed this

Seventh Day of December, 1999

*Attest:*

Q. TODD DICKINSON

*Attesting Officer*   *Acting Commissioner of Patents and Trademarks*